United States Patent
Hay et al.

(10) Patent No.: US 11,564,393 B2
(45) Date of Patent: Jan. 31, 2023

(54) FATTY AMMONIUM SALT STARCH COMPLEXES AS ANTIMICROBIALS, PLANT WOUND, AND WOOD PROTECTANTS

(71) Applicant: The United States of America, as represented by the Secretary of Agriculture, Washington, DC (US)

(72) Inventors: William T. Hay, Peoria, IL (US); Gordon W. Selling, Dunlap, IL (US); George F. Fanta, Morton, IL (US); Fred J. Eller, Peoria, IL (US)

(73) Assignee: The United States of America, as represented by The Secretary of Agriculture, Washington, DC (US)

( * ) Notice: Subject to any disclaimer, the term of this patent is extended or adjusted under 35 U.S.C. 154(b) by 98 days.

(21) Appl. No.: 16/028,849

(22) Filed: Jul. 6, 2018

(65) Prior Publication Data

US 2019/0014780 A1    Jan. 17, 2019

Related U.S. Application Data

(60) Provisional application No. 62/531,034, filed on Jul. 11, 2017.

(51) Int. Cl.
*A61L 15/28*  (2006.01)
*A61L 15/42*  (2006.01)
*A01N 43/16*  (2006.01)

(52) U.S. Cl.
CPC .............. *A01N 43/16* (2013.01); *A61L 15/28* (2013.01); *A61L 15/42* (2013.01); *A61L 2300/404* (2013.01)

(58) Field of Classification Search
None
See application file for complete search history.

(56) References Cited

U.S. PATENT DOCUMENTS

| | | | | |
|---|---|---|---|---|
| 6,780,903 B2 * | 8/2004 | Peltonen | ..................... | C08J 3/03 524/297 |
| 10,072,381 B2 * | 9/2018 | Fanta | ..................... | D21H 23/22 |
| 2002/0015854 A1 * | 2/2002 | Billmers | ................. | D21H 19/12 428/500 |
| 2010/0068543 A1 * | 3/2010 | Hayward | .................. | C08H 8/00 427/393 |

OTHER PUBLICATIONS

Fanta et al., "Films prepared from poly(vinyl alcohol) and amylose-fatty acid salt inclusion complexes with increased surface hydrophobicity and high elongation", Research Article, 68, 874-884, Jan. 15, 2016 (Year: 2016).*

Fanta et al., "Preparation and properties of amylose complexes prepared from hexadecylamine and its hydrochloride salt", Carbohydrate Polymers, 98, 555-561, 2013 (Year: 2013).*

Fanta, George F. et al., "Poly(vinyl alcohol) composite films with high percent elongation prepared from amylose-fatty ammonium salt inclusion complexes," Journal of Applied Polymer Science, (2016), 44110 (1-8).

Pour, Zahra Sekhavat et al., "Performance properties and antibacterial activity of crosslinked films of quaternary ammonium modified starch and poly(vinyl alcohol)," International Journal of Biological Macromolecules, (2015), 80:596-604.

Hay, William T. et al., "Rheological characterization of solutions and thin films made from amylose-hexadecylammonium chloride inclusion complexes and polyvinyl alcohol," Carbohydrate Polymers, (2017), 161:140-148.

Hay, William T. et al., "Effect of spray drying on the properties of amylose-hexadecylammonium chloride inclusion complexes," Carbohydrate Polymers, (2016), 157:1050-1056.

Eller, F.J. et al., "Hexadecyl ammonium chloride amylose inclusion complex to emulsify cedarwood oil and treat wood against termites and wood-decay fungi," International Biodeterioration & Biodegradation, (2018), 129:95-101.

International Searching Authority, PCT/US2018/041285 for the United States of America, as Represented by the Secretary of Agriculture, International Filing Date Jul. 9, 2018, AG010017-PCT.

* cited by examiner

*Primary Examiner* — Robert T. Crow
*Assistant Examiner* — John P Nguyen
(74) *Attorney, Agent, or Firm* — John D. Fado; Mark D. McNemar

(57) ABSTRACT

Provided herein are fatty-ammonium salt/starch inclusion complexes comprising one or more of a variety of fatty amines. Such complexes can be combined with film-forming agents, such as poly(vinyl) alcohol (PVOH) and plasticizing agents. The inclusion complexes of the present invention can be utilized as antimicrobial agents, preventing microbial growth on organic and inorganic surfaces. In specific embodiments, inclusion complexes of the present invention are applied to vegetable or fruit surfaces in order to impede microbial growth. Inclusion complexes of the present invention can be applied to wood in order to impede microbial growth and insect consumption and to wound dressings.

14 Claims, 7 Drawing Sheets
(2 of 7 Drawing Sheet(s) Filed in Color)

FATTY AMMONIUM SALT STARCH COMPLEXES AS ANTIMICROBIALS, PLANT WOUND, AND WOOD PROTECTANTS

BACKGROUND OF THE INVENTION

Field of Invention

Provided herein are fatty-ammonium salt/starch inclusion complexes comprising one or more of a variety of fatty amines. Inclusion complexes can be combined with film-forming agents, such as poly(vinyl) alcohol (PVOH) and plasticizing agents. The inclusion complexes of the present invention can be utilized as antimicrobial agents, preventing microbial growth on treated surfaces. In specific embodiments, inclusion complexes of the present invention are applied to vegetable or fruit surfaces in order to impede microbial growth, or applied to wood to impede microbial growth and insect consumption.

Background

Starch is an inexpensive, biodegradable plant based polysaccharide that has a large number of applications in food and material science. Starch is composed of repeating glucose units and is comprised of two fractions, amylose and amylopectin. The amylose fraction is a linear polysaccharide with α-(1→4)-glucan linkages, while the amylopectin fraction is a highly branched α-(1→4)-glucan with α(1→6)-branch points (Tester et al., J. Cereal Sci., (2004) 39:151). Amylopectin is typically the major component of normal food grade corn starch, with amylose typically constituting 15-30% of the starch. Starches containing greater than 40% amylose are defined as high-amylose starches, while starches containing <1% amylose are defined as waxy starches (Bates et al., J. Am. Chem. Soc., (1943) 65:142).

When dissolved, amylose can form inclusion complexes with hydrophobic ligands such as fatty acids and fatty amines (Godet et al., J. Food Sci., (1996) 61:1196; Helbert & Chanzy, J. Biol. Macromolecules, (1994) 16:207; Obiro et al., Food Rev. Int'l., (2012) 28:412)). The left-handed helices formed by amylose in solution have a hydrophobic internal cavity where hydrophobic ligands can reside (Saenger, Naturwissenschaften (1984) 71:31). Structurally, the inner surface of the helix is comprised of methylene groups and glycosidic linkages, while the hydrophilic hydroxyl groups are located on the outer surface (Immel & Lichtenthaler, Flexible and Rigid Non-Glucose Cyclooligosaccharides: Synthesis, Structure, and Properties, (2000) 52:27; Obiro et al., supra). In the presence of suitable ligands, amylose-inclusion complexes can form when the hydrophobic portion of a ligand associates with the hydrophobic internal cavity of the amylose helix by van der Waals forces (Nimz, et al., Carbohydr. Res., (2004) 339:1427). Previous studies have suggested that a minimum chain length of 10 carbons is necessary for complex formation, with an ideal chain length between 14 and 18 carbons (Godet et al., Int'l J. Biol. Macromolecules, (1995); Krog N., Starch/Stärke, (1971) 23:206).

Amylose-inclusion complexes are categorized into two main types, type I and type II. Type I complexes are randomly oriented structures with no distinct crystalline regions. They are typically formed at lower temperatures (<90° C.) and are partially ordered. Type II complexes are semicrystalline with distinct crystalline and amorphous regions and are formed at temperatures near 90° C. (Biliaderis & Seneviratne, Polymers, (1990) 13:185; Tufvesson & Eliasson, Carbohydr. Polymers, (2000) 43:359). Amylose-inclusion complexes can be produced using microwave processing (Felker et al., Starch/Stärke, (2013) 65:864) or the commonly used industrial method of steam jet cooking (Klem & Brogly, Pulp and Paper, (1981) 98-103). Using this technique, water dispersions of granular starch are heated at high temperature with high-pressure steam under high-shear conditions to dissolve the starch. The desired ligand is then added to the resulting starch solution to form the amylose inclusion complex (Fanta et al., Carbohydr. Polymers, (1999) 38:1). While fatty acid inclusion complexes produced in this fashion will form insoluble spherulites when cooled, amylose-fatty acid salt inclusion complexes are water soluble and can be dried and easily re-dissolved in water (Fanta et al., Carbohydr. Polymers, (2010) 81:645; Fanta et al., Carbohydr. Polymers, (2013) 98:555)).

The formation of amylose inclusion complexes with N-hexadecylammonium chloride using steam jet cooking and isolation using freeze drying has been previously described (Fanta et al., Carbohydr. Polymers, (2013) 98:555). Alternatively, spray drying can be used to isolate the amylose complexes (Hay et al., Carbohydr. Polymers, (2017) 161:140). A $6_1$V x-ray diffraction pattern is observed after complex formation, as well as an inhibition of retrogradation due to electrostatic repulsion between amylose helices. Blending the water soluble amylose N-hexadecylammonium chloride complexes (Hex-Am) with polyvinyl alcohol (PVOH) has been demonstrated to produce composite films with high tensile strength, high % elongation and increased water contact angle (Fanta et al. I, J. Appl. Polymer Sci., (2016) DOI 10.1002/APP.44110; Fanta et al. II, Starch/Stärke, (2016) 68:874). Alternatively, these complexes can be made using microwave techniques (Felker et al. Starch/Stärke (2013) 65:864) utilizing microwave irradiation to provide the necessary thermal energy to gelatinize the starch and allow complex formation to occur.

Presented herein, we provide new uses as antimicrobial agents for fatty-ammonium-starch inclusion complexes. Also provided herein are novel formulations of these inclusion complexes with film-forming agents, such as PVOH and uses for these films.

SUMMARY OF THE INVENTION

Provided herein, in one embodiment, is a method of decreasing microbial growth on a surface, by applying an effective amount of a fatty-ammonium salt polysaccharide inclusion complex to the surface and allowing a microbe to come into contact with said inclusion complex under conditions supporting growth of the microbe, thereby decreasing growth of the microbe. In some instances, the polysaccharide portion of the inclusion complex is amylose (such as from high amylose corn starch) or dextrin. In any embodiment provided herein, the fatty amine portion of the inclusion complex is derived from one or more fatty ammonium salts, where each fatty ammonium salt comprises eight to twenty-two carbons in at least one chain attached to a nitrogen. In some embodiments, the one or more fatty ammonium salts comprise twelve to eighteen carbons. In still other embodiments, the fatty amine portion of the inclusion complex is an amine with two carbon chains attached to a nitrogen and the two chains have eight carbons or less and the total number of carbons in the amine is at least twelve. Amines used to derive ammonium salts useful in some embodiments of such methods can be primary, secondary or tertiary. In some embodiments where the amine is a secondary or tertiary amine comprising a first chain of twelve or more carbons, the second and third alkyl groups attached to the nitrogen have three or fewer carbons and the second and third alkyl groups do not have hydroxyl groups. Fatty-ammonium salts useful in the present invention can contain chloride, bromide or sulfate counter ions. In particular embodiments, the specific fatty-ammonium salt utilized is N-octadecylammonium chloride, N-dodecylammonium chloride, N,N-didecyl-N-methylammonium chloride, N-tetradecylammonium chloride, N-hexadecylammonium chloride, N,N-dioctylammonium chloride, N-dodecylanilium chloride, N-methyloctadecylammonium chloride, N,N-dimethyl-N-hexadecylammonium chloride, N,N,N-trimethyl-N-tetradecylammonium chloride, N-hexadecyl-N,N,N-trimethylammonium bromide, benzethonium chloride, N-hexadecylpyridinium chloride, or laurylcholine chloride. In a specific embodiment, the fatty-ammonium salt is N-hexadecylammonium chloride and is present at a concentration of 3-9% of the polysaccharide portion of the inclusion complex. For these particular embodiments, the polysaccharide portion of the inclusion complex can be amylose. These methodologies can be utilized to control microbial growth of bacteria, fungi, or both. The treated surfaces can be present on plants, fruits, and vegetables, including wound surfaces. Treated surfaces can also be present on wood, such as to limit growth of fungi. In any of these embodiments, the inclusion complexes of the present invention also comprise a film-forming agent, such as PVOH. Methodologies utilizing film-forming agents can also include the use of plasticizers, such as glycerol, sorbitol, lactic acid, polyethylene glycol, ethyl lactate, salicylic acid, or a combination thereof.

Also provided herein are compositions comprising a plant, fruit or vegetable and a fatty-amine polysaccharide inclusion complex. In some instances, the polysaccharide portion of the inclusion complex is amylose (such as from high amylose corn starch) or dextrin. In any embodiment of such compositions provided herein, the fatty amine portion of the inclusion complex can be derived from one or more fatty ammonium salts, where each fatty ammonium salt comprises eight to twenty-two carbons in at least one chain attached to a nitrogen. In some embodiments, the one or more fatty ammonium salts comprise twelve to eighteen carbons. In still other embodiments, the fatty amine portion of the inclusion complex is an amine with two carbon chains attached to a nitrogen, the two chains have eight carbons or less, and the total number of carbons in the amine is at least twelve. Amines used to derive ammonium salts useful in some embodiments of such methods can be primary, secondary or tertiary. In some embodiments where the amine is a secondary or tertiary amine comprising a first chain of twelve or more carbons, the second and third alkyl groups attached to the nitrogen have three or fewer carbons and the second and third alkyl groups do not have hydroxyl groups. Fatty-ammonium salts useful in the present invention can contain chloride, bromide or sulfate counter ions. In particular embodiments, the specific fatty-ammonium salt utilized is N-octadecylammonium chloride, N-dodecylammonium chloride, N,N-didecyl-N-methylammonium chloride, N-tetradecylammonium chloride, N-hexadecylammonium chloride, N,N-dioctylammonium chloride, N-dodecylanilium chloride, N-methyl-N-octadecylammonium chloride, N,N-dimethyl-N-hexadecylammonium chloride, N,N,N-trimethyl-N-tetradecylammonium chloride, N-hexadecyl-N,N,N-trimethylammonium bromide, benzethonium chloride, N-hexadecylpyridinium chloride, or N-laurylcholine chloride. In a specific embodiment, the fatty-ammonium salt is N-hexadecylammonium chloride and is present at a concentration of 3-9% of the polysaccharide portion of the inclusion complex. For these particular embodiments, the polysaccharide portion of the inclusion complex can be amylose. In any of these embodiments, the inclusion complexes can also contain a film-forming agent, such as PVOH and can also include plasticizers, such as glycerol, sorbitol, lactic acid, polyethylene glycol, ethyl lactate, salicylic acid, or a combination thereof.

In still another embodiment of the invention provided herein is a composition comprising wood and a fatty-amine polysaccharide inclusion complex. In some instances, the polysaccharide portion of the inclusion complex is amylose (such as from high amylose corn starch) or dextrin. In any embodiment of such compositions provided herein, the fatty amine portion of the inclusion complex can be derived from one or more fatty ammonium salts, where each fatty ammonium salt comprises eight to twenty-two carbons in at least one chain attached to a nitrogen. In some embodiments, the one or more fatty ammonium salts comprise twelve to eighteen carbons. In still other embodiments, the fatty amine portion of the inclusion complex is an amine with two carbon chains attached to a nitrogen, the two chains have eight carbons or less, and the total number of carbons in the amine is at least twelve. Amines used to derive ammonium salts useful in some embodiments of such methods can be primary, secondary or tertiary. In some embodiments where the amine is a secondary or tertiary amine comprising a first chain of twelve or more carbons, the second and third alkyl groups attached to the nitrogen have three or fewer carbons and the second and third alkyl groups do not have hydroxyl groups. Fatty-ammonium salts useful in the present invention can contain chloride, bromide or sulfate counter ions. In particular embodiments, the specific fatty-ammonium salt utilized is N-octadecylammonium chloride, N-dodecylammonium chloride, N,N-didecyl-N-methylammonium chloride, N-tetradecylammonium chloride, N-hexadecylammonium chloride, N,N-dioctylammonium chloride, N-dodecylanilium chloride, N-methyloctadecylammonium chloride, N,N-dimethlyhexadecylammonium chloride, N,N,N-trimethyl-N-tetradecylammonium chloride, N-hexadecyl-N,N,N-trimethylammonium bromide, benzethonium chloride, N-hexadecylpyridinium chloride, or N-laurylcholine chloride. In a specific embodiment, the fatty-ammonium salt is N-hexadecylammonium chloride and is present at a concentration of 3-9% of the polysaccharide portion of the inclusion complex. For these particular embodiments, the polysaccharide portion of the inclusion complex can be amylose. In any of these embodiments, the inclusion complexes can also contain a film-forming agent, such as PVOH and can also include plasticizers, such as glycerol, sorbitol, lactic acid, polyethylene glycol, ethyl lactate, salicylic acid, or a combination thereof.

In yet another embodiment, the present disclosure provides a method of decreasing insect consumption of wood, by exposing a wood eating insect (such as a termite) to any of the compositions comprising wood and a fatty-amine polysaccharide inclusion complex described herein under conditions which the insect would normally consume some or all of the wood, thereby decreasing the consumption of the wood as compared to wood lacking a fatty-amine polysaccharide inclusion complex.

The present disclosure also provides another embodiment of the invention which is a composition comprising a wound dressing and a fatty-amine polysaccharide inclusion body. Exemplary wound dressings include medical gauze and bandages.

INCORPORATION BY REFERENCE

All publications, patents and patent applications mentioned in this specification are herein incorporated by reference to the same extent as if each individual publication, patent or patent application was specifically and individually indicated to be incorporated by reference.

BRIEF DESCRIPTION OF THE DRAWINGS

The patent application file contains at least one drawing executed in color. Copies of this patent or patent application publication with color drawing(s) will be provided by the Office upon request and payment of the necessary fee.

The novel features of the invention are set forth with particularity in the claims. Features and advantages of the present invention are referred to in the following detailed description, and the accompanying drawings of which:

DETAILED DESCRIPTION OF THE INVENTION

Figure 1:
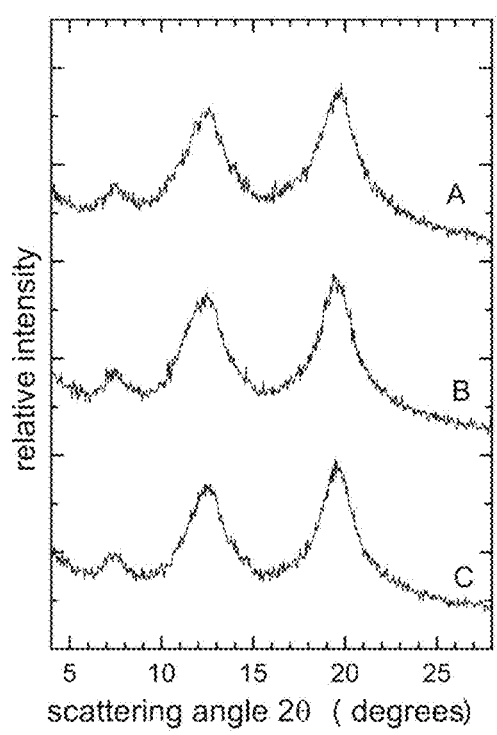
FIG. 1 provides x-ray diffraction patterns of starch complexes prepared with (A) N-dodecylammonium chloride ($C_{12}$), (B) N-hexadecylammonium chloride ($C_{16}$), and (C) N-octadecylammonium chloride ($C_{18}$).

Provided herein, in one embodiment, are fatty-ammonium salt-starch inclusion complexes that can be utilized as antimicrobial agents. Inclusion complexes of the present invention can be made with fatty amines having variable carbon chain lengths from about 8 carbons long to 22 carbons long, and mixtures thereof. Complexes of the present invention can utilize primary, secondary, tertiary, and quaternary amines, or a combination of these. Inclusion complexes in some embodiments can be combined with film-forming agents, such as PVOH, with or without additional components such as plasticizers. Further provided herein are methodologies for using fatty-ammonium salt-starch inclusion complexes as antimicrobial agents and as deterrents to wood-consuming insects such as termites.

Preferred embodiments of the present invention are shown and described herein. It will be obvious to those skilled in the art that such embodiments are provided by way of example only. Numerous variations, changes, and substitutions will occur to those skilled in the art without departing from the invention. Various alternatives to the embodiments of the invention described herein may be employed in practicing the invention. It is intended that the included claims define the scope of the invention and that methods and structures within the scope of these claims and their equivalents are covered thereby.

Technical and scientific terms used herein have the meanings commonly understood by one of ordinary skill in the art to which the instant invention pertains, unless otherwise defined. Reference is made herein to various materials and methodologies known to those of skill in the art. Any suitable materials and/or methods known to those of skill can be utilized in carrying out the instant invention. Materials and/or methods for practicing the instant invention are described. Materials, reagents and the like to which reference is made in the following description and examples are obtainable from commercial sources, unless otherwise noted.

As used in the specification and claims, use of the singular "a", "an", and "the" includes plural references unless the context clearly dictates otherwise.

The term "about" is defined as plus or minus ten percent of a recited value. For example, about 1.0 g means 0.9 g to 1.1 g and all values within that range, whether specifically stated or not.

The term "effective amount" of a composition provided herein refers to the amount of the composition capable of performing the specified function for which an effective amount is expressed. The exact amount required can vary from composition to composition and from function to function, depending on recognized variables such as the compositions and processes involved. An effective amount can be delivered in one or more applications. Thus, it is not possible to specify an exact amount, however, an appropriate "effective amount" can be determined by the skilled artisan via routine experimentation.

The term "antimicrobial", and grammatical variations thereof, refers to the ability of a composition of the present invention to impede growth of a microorganism, or kill a microorganism, when present in an effective amount. "Antibacterial" and "antifungal" refer specifically to the capability of a composition to impede growth of, or kill, bacteria and fungi, respectively, when present in an effective amount. All of these terms include organisms (e.g., basidiomycete fungi) that exhibit both microscopic and macroscopic growth.

Fatty Amine/Polysaccharide (Starch) Inclusion Complexes

Fatty amines utilizable in practicing the inventions disclosed herein include primary, secondary, tertiary and quaternary amines. They can be derived from natural sources, or be made synthetically. Such fatty amines can have carbon chains from about 8 carbons long to 22 carbons long, including 8, 9, 10, 11, 12, 13, 14, 15, 16, 17, 18, 19, 20, 21, and 22 carbon atoms, and mixtures thereof. Preferred embodiments include primary ammonium salts with between twelve and eighteen carbons. The most preferred ammonium salt is N-hexadecylammonium chloride. Fatty amines can be utilized as any relevant salt including, but not limited to, chlorides, bromides, and sulfates. Fatty amines can be converted to ammonium salts in solution via the addition of equimolar amounts of suitable acid (e.g., hydrochloric acid). Alternatively the quaternary ammonium salt can be produced by reaction of a primary, secondary or tertiary amine with suitable amount of alkylating reagent (or other electrophilic process) under conditions which will give tetravalent nitrogen, e.g. an ammonium salt. When made in this fashion, the ammonium salt will not be able to readily convert back to the base by sensible modification of pH. In the formation of the fatty ammonium salts—starch complexes utilized to practice the embodiments disclosed herein, fatty ammonium salts can be added at about 1.5% to about 20% of the mass of starch. Preferably, the amount is between 3-10% fatty ammonium salt, and most preferably about 5% (roughly equivalent to 7.5% of the mass of the amylose component of the starch utilized).

In embodiments where branched fatty ammonium salts are utilized, preferred salts will have at least one carbon chain of ≥10 carbons attached to the nitrogen molecule. Functionalities (e.g., esters) can be present within the carbon chain of ≥10 carbons. Typically, wherein two or more alkyl chains are attached to the nitrogen molecule of the fatty amine, each of the chains are ten or fewer carbons in length and, preferably, the fatty amine has a total of sixteen carbons or less. Preferably, alkyl chains attached to the nitrogen of the fatty amine will not have hydroxyl groups. Fatty ammonium salt portions of inclusion complexes can comprise a mixture of fatty ammonium salts.

Any suitable polysaccharide can be utilized in making the fatty ammonium salt-polysaccharide complexes of the present invention. In preferred embodiments, the polysaccharide is a starch comprising predominantly α-(1→4)-glucan linkages, such as amylose (commonly found in plant starches, such as corn and wheat starch), waxy corn starch, potato starch, wheat starch, rice starch, and tapioca starch, or dextrins (dextrin, dextrin 2, dextrin 3). Amylose utilized in making the fatty ammonium salt—amylose complexes of the present invention can range from 20-75% and can be from any suitable source (e.g., high amylose corn starch). Preferred embodiments utilize amylose from corn starch, where the percentage of amylose can vary from about 20-80%, with the remainder being amylopectin. The most preferred embodiments utilize high amylose corn starch (60-80% amylose).

Suitable polysaccharides preferably have sufficient linear non-branched repeat units to allow formation of a complex with a chosen fatty ammonium salt, as evidenced by the presence of two peaks in x-ray diffraction spectra of the complex where one peak is found between 12.5 and 13.5 2θ the other peak is found between 19.75 and 20.75 2θ (see, e.g., FIG. 1). In embodiments utilizing fatty quaternary ammonium salts, when 3-9% of the quaternary salt is combined with a chosen polysaccharide and thermally processed, the resulting complex can form at least a 3% solids solution with water.

Fatty-ammonium salt/amylose inclusion complexes are known in the art and are generally prepared by steam jet cooking and microwave preparation methodologies. Steam jet cooking of starch is generally described in the art (Klem & Brogley, supra). In such methodologies, a starch such as high amylose corn starch in water is passed through a steam jet cooker operating under excess steam conditions (Fanta et al., Carbohydr. Polymers, (2013) 98:555). Hot, jet cooked starch solutions are collected in a container. Solutions of fatty ammonium salts are prepared separately by dissolving the salt in water, or combining the fatty amine with an acid (e.g., HCl) in concentrations sufficient to convert the amine to its ammonium salt. Typically, the fatty ammonium salt solutions are heated (e.g., to 90° C.) to ensure maximum solubilization, and are then mixed with the hot starch solution. The combination is then cooled prior to drying, with freeze drying and spray drying being preferred drying methods. Specific steam jet and microwave methodologies are detailed in the Examples below, but any methodology known in the art can be utilized to form the inclusion complexes of the present invention.

Fatty-amine starch inclusion complexes can be applied to particular applications as is, or can be combined with any other component desired by a user including, but not limited to, film-forming agents and plasticizers.

Film-Forming Agents and Plasticizers

In some embodiments of the present invention, ammonium salt-amylose inclusion complexes are combined with film forming agents and/or plasticizers for particular applications. Polymers utilizable as film-forming agents can be any water soluble/dispersible (e.g., latex) polymer known in the art and can be natural, synthetic, linear, branched chain, crosslinked, network, elastomers, fibers, thermoplastic, thermosetting, or any other film-forming agent. Examples include poly (vinyl) alcohol, (PVOH), polyvinyl pyrrolidone, polyacrylic acid, polyethylene oxide, hydroxypropylmethyl cellulose, hydroxylpropyl cellulose, carboxymethyl cellulose, casein, gums (e.g., locust bean gum and guar gum), cationic starch, soluble starch and polyacrylamides. Preferred film-forming agents are water soluble, biodegradable and non-toxic and can be readily combined with the fatty-amine starch inclusion complexes of the present invention without significantly impinging their anti-microbial activities. In preferred embodiments of the present invention utilizing film-forming agents, PVOH is utilized as the film forming agent.

Plasticizers can be added to fatty-ammonium salt-amylose inclusion complexes, typically in the presence of film-forming agents. Many such substances are known in the art, and can readily be chosen by the skilled artisan to alter the physical properties of the inclusion complex films as desired. Exemplary, but non-limiting examples of such substances include glycerol, sorbitol, lactic acid, polyethylene glycol (200 m.w.), ethyl lactate and salicylic acid. Preferred plasticizers are miscible with the fatty-ammonium salt-amylose inclusion complexes and film-forming agents and do not interfere with the antimicrobial capabilities of the inclusion complexes.

Antimicrobial Applications

Many of the fatty-ammonium salt-amylose inclusion complexes of the present invention can be utilized as antimicrobial agents. Such inclusion complexes can be applied alone, or in formulations with film-forming agents and/or plasticizers. For embodiments in which the inclusion complexes are utilized as antimicrobial agents, the complexes can be applied to surfaces (e.g., wood, paper, fabrics, fruits and vegetables, plant wounds, countertops, metal, keyboards) to impede microbial growth. Where the complexes are applied to fruits or vegetables, they can be applied pre-harvest, or post-harvest. Inclusion complexes can be applied to surfaces prophylactically (e.g., to prevent future microbial growth). For example, inclusion complexes can be applied to the surfaces of vegetables such as seed potatoes before planting to inhibit microbial growth until the seed potato develops its own protective skin. Or it can be applied to surfaces contaminated with undesired microbial growth. One unexpected feature of antimicrobial inclusion complexes is that, when used to treat wood, it deters feeding by wood-consuming insects, such as termites. When used to treat wood, inclusion complexes can be combined with a solvent such as cedarwood oil at a concentration of 1-10%.

Inclusion complexes can be applied by spraying, coating, painting, dipping, soaking, or any other appropriate methodology to a surface of interest. As such, they can be combined with other components applicable to the method of application (e.g., combined with a propellant for spraying applications). Inclusion complexes of the present invention, can be formulated as aqueous compositions for application to a surface or item of interest. When using one of the preferred types of polysaccharide, high amylose corn starch, then aqueous solutions of 4.5% inclusion complex (w:v) or less are preferred. The concentration (% solids) of the aqueous solution will be dependent on the solubility and flow properties of the inclusion complex—much of which will be driven by the polysaccharide.

Generally, a fatty-ammonium salt-amylose inclusion complex will be applied to a surface or item of interest in an amount effective to impede 25-100% of microbial growth, as compared to untreated surfaces or items. As described in the Examples, the effective amount of any complex of the present invention can be determined by exposing one or more microbes to the complex and determining the minimum inhibitory concentration (MIC). In preferred embodiments, an inclusion complex of the present invention inhibits 50-100% of microbial growth when present in an effective amount.

Inclusion complexes of the present invention can also be incorporated into formulations for internal application, typically in the form of pills, tablets, capsules or powders. As such, the inclusion complexes can be combined with any pharmaceutically or veterinarily acceptable carrier known in the art. The complexes can also be combined with other components such as bactericides, fungicides, herbicides, pesticides, bait materials, colorants, odorants, and phagostimulants. Such additional components are well known in the art, and can readily be combined with the inclusion complexes of the present invention via standard methods.

Having generally described this invention, the same will be better understood by reference to certain specific examples, which are included herein to further illustrate the invention and are not intended to limit the scope of the invention as defined by the claims.

EXAMPLES

Example 1

Materials and Analytical Methodologies

High amylose corn starch with a reported amylose content of 68% (determined by iodine binding (Jane et al., Cereal Chem. (1999) 76:629)) was obtained from Cargill, Minneapolis, Minn.; N-dodecylamine (98%), N-hexadecylamine (98%), and N-octadecylamine (97%) from Sigma-Aldrich, St. Louis, Mo.; poly(vinyl alcohol) (PVOH) (MW 133,000, 99 mole % hydrolyzed) from Polysciences, Warrington, Pa.; and glycerol (Certified A.C.S.) from Fisher Scientific, Pittsburgh, Pa. The moisture contents of starch (9.4%) and PVOH (3.9%) were determined by weight loss after drying under vacuum for 4 hours at 100° C.

X-ray diffraction analysis was performed by Texray, Laboratory Services, Argyle. Tex., using the same procedure described previously (Fanta et al. II, supra).

Films were stored for five days at 23° C. and 50% relative humidity (RH) before tensile testing. Tensile strength, Young's modulus, and % elongation were obtained using an Instron Universal Testing Machine, Model 4201 (Canton, Mass.) according to the ASTM D638 Type V testing procedure (crosshead speed 10 mm/min, gauge length 7.62 mm, load cell 1 kN or 100 N). Significant differences between film properties were determined using an analysis of variance (n=5) and Duncan's multiple range test (P<0.05).

To measure contact angles, solutions of PVOH and the $C_{16}$ amylose complex were prepared at concentrations of 2% as described for the films prepared for tensile testing, and glycerol was added in amounts equal to 20% of the dissolved polymers. To obtain cast films with flat surfaces for contact angle determinations, 2 mL of each solution was transferred with a pipette to a 57×14×1 mm wax frame affixed to the surface of a 25×75×1.0 mm glass microscope slide coated with BYTAC adhesive film (Saint Gobain Performance Plastics, Poestenkill, N.J.). The solutions were air dried at room temperature. Measurements were conducted using axisymmetric dropshape analysis on a FTA-200) automated goniometer (First Ten Angstroms, Portsmouth, Va.) with fta32 v2.0 software, using the procedure described previously (Fanta et al. II, supra). The contact angles reported were those observed at 60 sec (mean of five measurements±standard deviation).

For light microscopy analysis, PVOH/amylose-starch complex film pieces were taped onto microscope slides and enclosed in a sealed Petri dish containing a small piece of moistened filter paper to provide humidity and dry iodine crystals, which stained the films with iodine vapor. Stained films were observed and photographed with a Zeiss Axioskop light microscope using an Axiocam ICc 3 digital camera (Carl Zeiss, Inc., Thornwood, N.Y.). For scanning electron microscopy (SEM), small pieces of the upper surfaces of the dried films were sputter-coated with gold and examined with a JSM-6010LA SEM (JEOL USA, Peabody, Md.).

Amylose-Fatty Ammonium Salt Complex Preparation.

The procedure used for steam jet cooking was the same as previously reported (Fanta et al., Carbohydr. Polymers, (2010) 81:645). A dispersion of 50.0 g of high amylose starch in 900 mL of deionized water was passed through a Penick & Ford (Penford Corp., Englewood, Colo.) laboratory model steam jet cooker operating under excess steam conditions (hydroheater temperature 140° C., steam back pressure 380 kPa (40 psig), steam line pressure 550 kPa (65 psig), and pumping rate 1 L/min) (Klein & Brogley, Pulp Pap., (1981) 55:98).

Solutions of the HCl salts of fatty amines were prepared by dispersing 2.6 g of fatty amine in 100 mL of deionized water solution with an HCl concentration equal to that required to convert the amine to its ammonium salt. This weight of fatty amine was equal to 7.5% of the weight of amylose in 50.0 g of high amylose corn starch. The acidified amine dispersions were then heated to 90° C. to obtain clear solutions. The hot solutions of fatty ammonium salts were then added to the hot starch dispersions. The dispersions were blended for 1 min and then cooled in ice water to 25° C. The amylose-ammonium salt complex was then isolated by freeze-drying. The amylopectin component of high amylose corn starch was not separated from the amylose complexes, since removal of amylopectin would not be practical in a commercial process.

Water solubility of the freeze-dried amylose-ammonium salt complexes was determined by heating dispersions of 2 g of complex in 98 mL of water to 80° C. followed by cooling in ice water to 25° C. The cooled dispersions were centrifuged for 1 hour at 10.000 rpm (15,317 g) in a Sorvall Legend centrifuge equipped with a Fiber-lite F14-6X250 rotor (Thermo Fisher Scientific, Hanover Park, Ill.). Pellets were washed with 50 mL of fresh water and centrifuged again. The percentages of water insoluble materials based on the weights of freeze-dried settled solids were 8.0%, 1.1%, and 0.5% for the complexes prepared from the HCl salts of N-dodecylamine ($C_{12}$), N-hexadecylamine ($C_{16}$), and N-octadecylamine ($C_{18}$), respectively.

When the freeze-dried complexes were dissolved in water for film preparation, the amount of insoluble material remaining in the solutions was largest for the $C_{12}$ complex (8.0%), whereas smaller amounts of insoluble material (1.1% and 0.5%) were observed when the complexes were prepared from the $C_{16}$ and $C_{18}$ ammonium salts. The relatively high percentage of insoluble material obtained for the $C_{12}$ complex could be caused by less complex formation due to the lower molecular weight and increased water solubility of the $C_{12}$ fatty ammonium salt (Putseys et al., J. Cereal Sci., (2010) 51:238). A lesser amount of complex formation could result in retrogradation of partially complexed amylose and could thus account for the increased percentage of water insoluble material observed.

Figure 2:
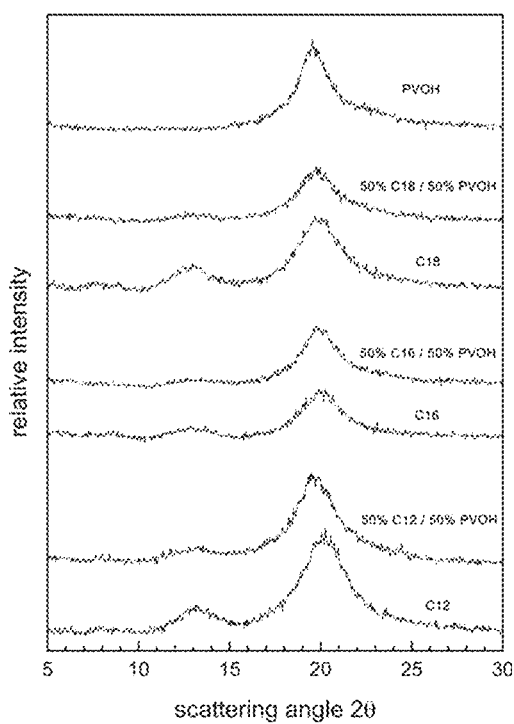
FIG. 2 provides x-ray diffraction patterns of films prepared from PVOH, amylose-N-dodecylammonium chloride complexes ($C_{12}$), amylose-N-hexadecylammonium chloride complexes ($C_{16}$), amylose-N-octadecylammonium chloride complexes ($C_{18}$), and 50:50 mixtures of PVOH and the three complexes.

X-ray diffraction patterns of the freeze-dried, water soluble products (FIG. 1) showed similar $6_1V$ reflections at 7.5°. 12.5°, and 20° 2θ confirming the formation of amylose inclusion complexes from the three fatty ammonium salts. The scattering pattern of the 8.0% water insoluble fraction isolated from the solution of the $C_{12}$ (N-dodecylammonium chloride) complex prepared for film casting (not shown) also showed $6_1V$ reflections similar to those shown in FIG. 1 for the water-soluble fraction. FIG. 2 shows the X-ray diffraction patterns of films prepared from 100% PVOH, 50:50 mixtures of PVOH and the three amylose-ammonium salt complexes, and the three amylose-ammonium salt complexes in the absence of PVOH. Comparison of the diffraction patterns in FIG. 1 and FIG. 2 show that the freeze-dried complexes remained intact and were not adversely affected when dissolved in hot water, blended with PVOH, and allowed to dry to form composite films.

Microwave Production of Amylose-Complexes

An Ethos 1600 (Milestone Inc., Monroe, Conn.) microwave reactor oven was used to irradiate ~3% solids (m/m) mixtures of starch and various ligands in deionized water. The ligand was either a pre-made fatty ammonium chloride salt or a fatty amine which was added to the starch, followed by an equal molar amount of 1.035 M HCl.

Specific quantities are detailed for each Example. The reactor vessel was a sealed 270 mL perfluoroalkoxy Teflon® reactor vessel (Milestone Inc. product code 45161T) and continuously stirred using a Teflon® magnetic stir bar at maximum speed. The sample must be heated sufficiently to gelatinize the starch, in this work the sample was heated from 0 to 120° C. in 1.5 min, 120 to 140° C. in 1.5 min after which the reaction vessel was cooled to 100° C. and maintained at 100° C. for 60 min. The reactor vessel was then cooled in an ice bath until the sample reached room temperature. Samples were then centrifuged for 20 minutes at 1,400×g and the supernatant was collected and freeze dried using a Labconco Freezone 6 Liter freeze dryer (Labconco, Kansas City, Mo.).

Example 3

PVOH and Amylose-Fatty Ammonium Salt Complex Films.

Preparation

PVOH and freeze-dried amylose-fatty ammonium salt complexes were dissolved in deionized water at concentrations of 2% (dry basis), and the stirred dispersions were heated to 80° C. The solutions were then immediately cooled in ice water to 25° C. Amylose-ammonium salt complexes are acidic (pH of a 2% solution of the $C_{16}$ complex was 3.6), so an experiment was carried out to determine whether acid hydrolysis of complexed amylose occurs under the conditions used to dissolve the complexes for film preparation. The $C_{16}$ ammonium salt complex was dissolved as described above and the viscosity of the solution was determined using an ARES LS1 rheometer (TA Instruments, New Castle, Del.) with 50 mm titanium parallel plate geometry. The sample was then reheated to 80° C. and stirred at 100 $sec^{-1}$ for 1 hour using an AR 2000 rheometer (TA Instruments, New Castle, Del.) with concentric cylinder geometry. This rheometer was used to reheat the sample because the container could be sealed to avoid loss of water that would affect the observed viscosity. The viscosity of the reheated and cooled solution was then determined at 25° C. and 100 $sec^{-1}$ using the ARES LS1 rheometer as described above and compared with the measurements obtained with the AR 2000 rheometer. The experiment was run in duplicate and the viscosity was determined in triplicate with the ARES LS1 rheometer. The t-test analysis showed that there was no significant difference in the viscosities of the initially prepared sample and the sample that was stirred at 80° C. for 1 h, indicating that amylose was not hydrolyzed under the conditions used to dissolve the freeze-dried samples.

Various portions of 2% solutions of PVOH and amylose-ammonium salt complex were combined to obtain a series of 100 g solutions that contained amylose complex and PVOH in ratios of 100:0, 80:20, 70:30, 60:40, 50:50, 40:60, 30:70, 20:80, and 0:100. Glycerol (0.4 g), a commonly used plasticizer for starch, was added to give glycerol concentrations of 20% based on total polymer solids, and entrapped air was removed by applying vacuum to the solutions at room temperature. The dispersions were then poured into a 12.5×17.8×0.4 cm rubber frame on a glass plate coated with BYTAC non-stick adhesive film (Saint Gobain Performance Plastics, Poestenkill, N.J.) and the dispersions were allowed to dry at room temperature.

Analysis of Physical Characteristics

PVOH composite films prepared from the $C_{16}$ ammonium salt complex were stained with iodine vapor to determine whether the amylose complex and PVOH components of the dried films separated into distinct phases, as previously observed for PVOH composite films prepared from the amylose-sodium palmitate complex (Fanta et al. II, supra). Films prepared from the $C_{16}$ ammonium salt complex were used as representative examples of these composite films, since the $C_{16}$ carbon chain is approximately midway between the chain lengths of the other two fatty amine salts used. Microscopic examination of films exposed to iodine vapor revealed uniform staining with no evidence of phase separation or starch-rich areas. This observation is in marked contrast to films prepared with the amylose-sodium palmitate complex, in which distinct starch-rich domains were seen from 20% to 60% content of the sodium palmitate complex (Fanta et al. II, supra). This lack of phase separation of the amine salt complex indicates a more intimate mixing of PVOH and the amylose complex, and suggests that ionic bonding of the cationic amine salt complex with the hydroxyl groups of PVOH and starch immobilizes the complex and prevent its coalescence into starch-rich domains upon film drying. Although it was observed with the sodium palmitate complex that the starch-rich domains remained strongly associated with PVOH and co-stretched with PVOH without separation to provide enhanced elongation (Fanta et al. II, supra), the more intimate mixing and ionic bonding that takes place between the cationic amylose complexes and the hydroxyl groups of PVOH results in composite films with even higher values for % elongation as described below.

Films prepared from 100% PVOH, 100% $C_{16}$ ammonium salt complex, and 100% sodium palmitate complex were simultaneously stained with iodine vapor. The films prepared from PVOH, the ammonium salt complex, and the sodium palmitate complex were pale yellow, medium pink, and dark blue, respectively. The pink color of the vapor-stained film prepared from the ammonium salt complex was unexpected, since the amylose-sodium palmitate complex showed the dark blue staining typically observed for amylose. The difference in color may be due to the different ionic charges of the head groups of the two complexed ligands. With the anionic sodium carboxylate head group, the complexed sodium palmitate would be held within the amylose helix solely by the interaction of the hydrophobic alkyl chain with the hydrophobic interior of the amylose helix, and the negative charge of the head group would to some extent be repelled by the slight negative charge of the hydroxyl groups of starch. The anionic sodium carboxylate complex could thus be more easily displaced by the polyiodide forms of dissolved iodine. including the longer polyiodides that impart the blue stain (Saibene & Seetharaman, Carbohydr. Polymers. (2006) 64:539; John et al., Carbohydr. Res., (1983) 119:254). However, with the $C_{16}$ ammonium salt complex, ionic association between the cationic head groups and the hydroxyl groups of starch would make the complexed ammonium salt relatively immobile and could thus inhibit its separation from the amylose helix. This could result in fewer long, empty zones in the amylose helix, and more abundant shorter helical zones available for binding with the shorter poly-iodide chains, which would impart more of a red color to the complexed amylose (Saibene & Seetharaman, supra; John et al., supra).

PVOH composite films prepared with 20% and 50% of the $C_{16}$ ammonium salt complex were also examined by SEM, and the morphologies of the film surfaces were compared with those of the PVOH-sodium palmitate films prepared previously (Fanta et al. II, supra) with the same percentages of amylose complex. Although protrusions were observed on the surfaces of films prepared from the sodium palmitate complex, films prepared from the ammonium salt complex were smooth, and no protrusions were observed, in agreement with the absence of phase separation observed by light microscopy.

Analysis of Tensile Properties

Figure 3:
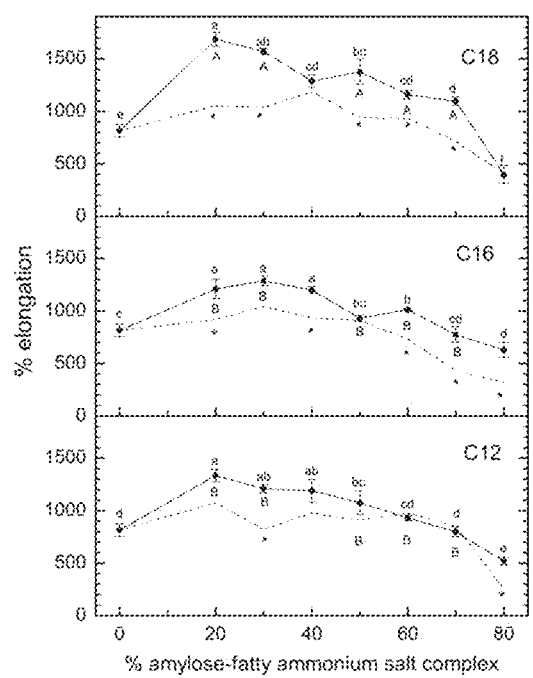
FIG. 3 provides percent elongation of films prepared with PVOH and increasing content of amylose-fatty ammonium chloride complexes ($C_{18}$, $C_{16}$, and $C_{12}$). Lower case letters designate significant differences among the levels of each complex type (horizontally). Upper case letters designate significant differences between ligands at each incorporation level (vertically). Dashed lines represent corresponding data obtained previously for the analogous carboxylic acid salt complexes (sodium stearate, palmitate, and laurate) for comparison. Asterisks designate significant differences (based on t-tests) between the cationic (solid lines) and anionic (dashed lines) ligands at each point.
Figure 4:
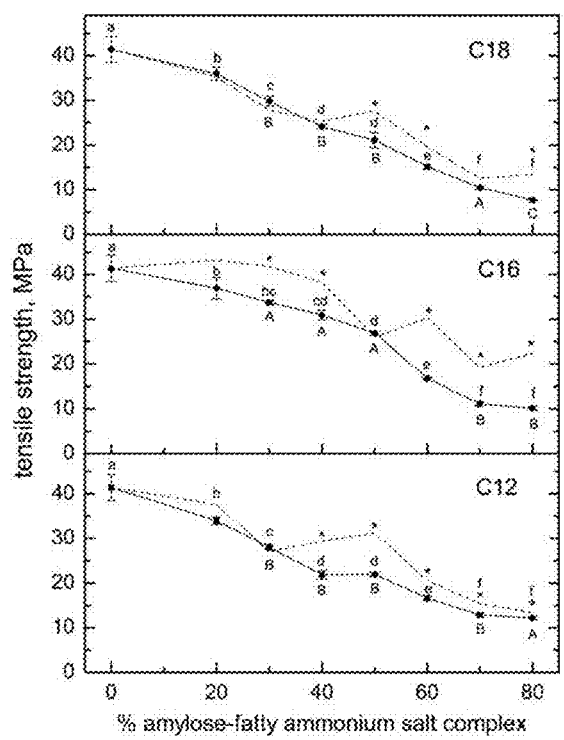
FIG. 4 provides tensile strength of films prepared with PVOH and increasing content of amylose-fatty ammonium chloride complexes ($C_{18}$, $C_{16}$, and $C_{12}$). Lower case letters designate significant differences among the levels of each complex type (horizontally). Upper case letters designate significant differences between ligands at each incorporation level (vertically). Dashed lines represent corresponding data obtained previously for the analogous carboxylic acid salt complexes (sodium stearate, palmitate, and laurate) for comparison. Asterisks designate significant differences (based on t-tests) between the cationic (solid lines) and anionic (dashed lines) ligands at each point.
Figure 5:
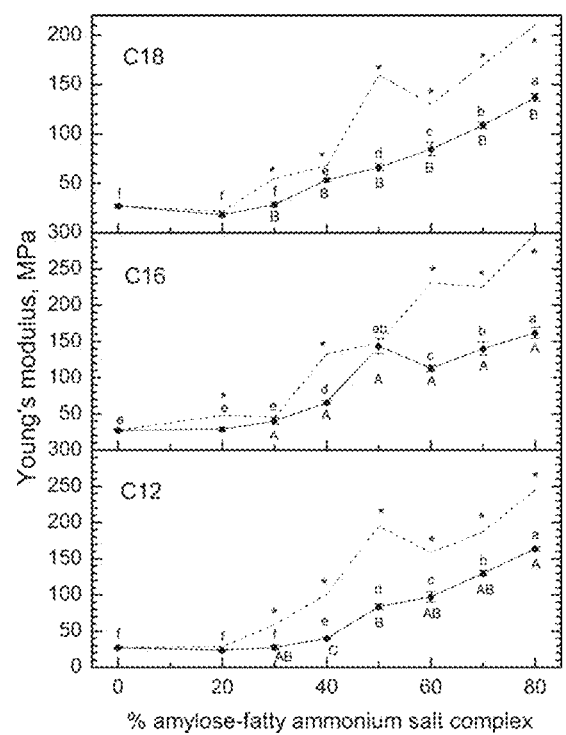
FIG. 5 provides Young's modulus of films prepared with PVOH and increasing content of amylose-fatty ammonium chloride complexes ($C_{18}$, $C_{16}$, and $C_{12}$). Lower case letters designate significant differences among the levels of each complex type (horizontally). Upper case letters designate significant differences between ligands at each incorporation level (vertically). Dashed lines represent corresponding data obtained previously for the analogous carboxylic acid salt complexes (sodium stearate, palmitate, and laurate) for comparison. Asterisks designate significant differences (based on t-tests) between the cationic (solid lines) and anionic (dashed lines) ligands at each point.

Values for percent elongation (% E), tensile strength (TS), and Young's modulus (YM) of PVOH composite films prepared from the $C_{18}$, $C_{16}$, and $C_{12}$ cationic amylose-fatty ammonium salt complexes are shown in FIGS. 3-5, respectively. The dashed curves in these figures show the tensile values previously obtained for films prepared in the same manner from anionic amylose-fatty acid salt complexes with the same carbon chain lengths (Fanta et al. II, supra). Differences between the tensile properties of films prepared from cationic and anionic complexes are likely due to differences in the manner in which these two types of complexes bind to PVOH and to each other when aqueous solutions of the polymers are allowed to dry. When composite films are prepared from anionic fatty acid salt complexes, hydrogen bonding between the negatively charged amylose complexes and PVOH, which also has a small negative charge density (Baueregger & Plank, J. Colloids Surf. Physicochem. Eng. Aspects. (2013) 434:145), will take place slowly as the concentration of the combined polymer solution increases due to evaporation of water at room temperature. This slow evaporation, coupled with the anionic repulsion between PVOH and the amylose-complexed fatty acid salt, allows the two components to separate before separation is inhibited by the increased viscosity of the aqueous solution. In contrast to the anionic fatty acid salt complexes, ionic bonding between the complexed cationic ammonium salt and the anionic hydroxyl groups of PVOH can take place in dilute water solutions, and this would inhibit the separation of the two polymers as the combined solutions are allowed to slowly dry.

Values for % E as high as those shown in FIG. 3 for the films prepared from the ammonium salt complexes have not been previously reported for PVOH composite films prepared from starch-based products. For example, cornstarch dissolved by stirring at 90-100° C. was combined with PVOH up to 10% starch yielding films with up to 230% E versus 200% E for pure PVOH (Siddaramaiah, et al., J. Appl. Polymer Sci., (2004) 91:630). Nanocrystals obtained from pea starch only slightly increased % E of PVOH from 710% E to about 740% E at 5% incorporation, while higher levels of nanocrystals and all levels of native pea starch granules resulted in decreased % E (Chen et al., Carbohydr. Polymers, (2008) 73:8). In the present study. % E more than doubled the value of the PVOH control (1687% E vs. 815% E) was observed with 20% incorporation of the $C_{18}$ ammonium salt complex, and for many of the films, the % E of the PVOH-ammonium salt complexes exceeded the % E of the control film prepared from 100% PVOH.

These high % E values, relative to those previously observed for films prepared from anionic fatty acid salt complexes (Fanta et al. II, supra) may be attributed to the stronger ionic bonding between PVOH and the cationic amine salt complexes. The highest values for % E were obtained for the series of films prepared from the $C_{18}$ ammonium salt complex, and the largest increase in % E was observed for the film prepared from an 80:20 mixture of PVOH and complex. The highest % E values for the films prepared from the $C_{18}$ complex could be due to the fewer number of cationic ammonium salt groups in this complex, since the same weight of fatty amine was used to prepare the three complexes, and the $C_{18}$ complex has the highest molecular weight. Fewer cationic amine groups in the complex would reduce the ionic association between the complex and PVOH (relative to the shorter chain-length ligands), and thus give more flexibility to the films and enhance their ability to stretch without breaking. The ability of the films to stretch without breaking could also be enhanced by the higher molecular weight of the complexed $C_{18}$ carbon chain.

FIG. 4 shows that the TS of films prepared from the cationic amylose-ammonium salt complexes was in most cases lower than the TS of comparable films prepared from the anionic fatty acid salt complexes (Fanta et al. II, supra), and declined steadily with increased percentages of the ammonium salt complexes. These results are consistent with the higher % E values for films prepared from the ammonium salt complexes because their increased ability to stretch before breaking results in a thinner film when it does break. As observed for the anionic complexes prepared from the sodium salts of fatty acids (Fanta et al. II, supra), the highest tensile strengths were observed when the composite films were prepared from the ammonium salt complex with the intermediate carbon chain length of $C_{16}$. The $C_{16}$ complex has a greater number of cationic ammonium groups than the $C_{18}$ complex due to its lower molecular weight, and can therefore ionically bond more tightly to PVOH to give the higher tensile strengths observed. Although the $C_{12}$ complex should theoretically have the greatest number of cationic ammonium groups, as discussed earlier, the increased water solubility of the $C_{12}$ ammonium salt and the shorter chain length could cause it to be less tightly bound within the hydrophobic interior of the amylose helix, which could have a negative effect on tensile strength.

As observed for the films previously prepared from anionic amylose-fatty acid salt complexes (Fanta et al. II, supra), FIG. 5 shows that the YM values for the films prepared from the cationic ammonium salt complexes increased with increasing percentages of complex: however, these values were lower than those observed when the films were prepared from fatty acid salt complexes. Since the YM pertains to the initial linear phase of the stress-strain curve before plastic deformation takes place, the lower YM values reflect the elasticity of these films before the yield point is reached. Typically, PVOH films have a much lower YM than the somewhat stiffer, more rigid starch films, and therefore an increase in YM with increasing content of the starch complexes would be expected. However, the YM increases more rapidly at higher levels of incorporation of the sodium carboxylate complexes (dashed lines, FIG. 5), while the increase is more gradual with the ammonium salt complexes (solid lines, FIG. 5). This difference may be related to the phase separation and phase inversion, which occurs with films prepared from the anionic carboxylate complex. Instead of the lower half of the curve increasing slowly with a sudden increase to higher values when the starch complex becomes the continuous phase, with the ammonium salt complexes there is no phase inversion because of the more complete mixing of the two components, and the single phase composition of these films retains more of the lower YM property of PVOH as the percentage of complex increases.

In summary, much higher % E values of PVOH composite films prepared from cationic amylose-ammonium salt complexes were observed compared to the % E values previously observed for films prepared from waxy corn starch (Fanta et al. II, supra) and the starches from various plant sources. The lower values for tensile strength observed would need to be weighed against the advantage that these films provide with respect to higher elongation, lower YM, and to the more rapid biodegradation and potentially lower cost due to the presence of the starch-based component.

Analysis of Surface Hydrophobicity

The surface contact angles of water droplets applied to films cast from mixtures of PVOH and $C_{16}$ ammonium salt complex with ratios from 100:0 to 0:100 are shown in Table 1. The film cast from 100% PVOH was the most hydrophilic film with a contact angle of 34.8°. The contact angle increased from 54.40 to 79.7° with increasing content of ammonium salt complex from 20% to 50%, and then remained essentially the same until dropping to 59.7° at 80% complex. The film prepared from 100% complex had a contact angle of 50.3°. These results are quite different from those observed for the series of films made with increasing contents of amylose-sodium palmitate complex (Fanta et al. II, supra), in which the contact angle increased from 31.7° for the PVOH control to 850 for films prepared with 20% sodium palmitate complex, and the values remained in the 80-89° range all the way up to 100% complex.

TABLE 1

Contact angles of dried films and pH of mixtures of Hex-Am/PVOH

| % Complex | % PVOH | Contact angle, degrees | pH |
| --- | --- | --- | --- |
| 0 | 100 | 34.8 ± 7.3$^e$ | 6.30 |
| 20 | 80 | 54.4 ± 6.4$^d$ | 5.63 |
| 30 | 70 | 65.8 ± 3.5$^b$ | 5.47 |
| 40 | 60 | 77.9 ± 1.9$^a$ | 5.60 |
| 50 | 50 | 79.7 ± 0.8$^a$ | 5.02 |
| 60 | 40 | 77.6 ± 0.9$^a$ | 4.79 |
| 70 | 30 | 75.1 ± 3.1$^a$ | 4.54 |
| 80 | 20 | 59.7 ± 0.7$^c$ | 4.23 |
| 100 | 0 | 50.3 ± 4.3$^d$ | 3.61 |

This difference in the response pattern can be attributed to the different effects of pH on the two ligands with opposite charges on the head groups. The PVOH solution had a pH of 6.30, and increasing the ratio of ammonium salt complex resulted in progressive acidification of the mixture to pH 3.61 (Table 1). The increase in pH with increased proportions of PVOH in the solution would therefore cause a partial conversion of the cationic ammonium salt head group of the complex to the uncharged amine form, which is more hydrophobic. At higher proportions of the complex, the pH is low enough for the complexes to remain in the cationic ammonium salt form, which is apparently more hydrophilic than the corresponding sodium palmitate complex as revealed by the higher contact angles observed in the former series of films. In contrast to the ammonium salt complex, solutions of sodium palmitate complexes are more alkaline than PVOH solutions (pH 8.2 for a 2% solution of the complex), and therefore the reduction in pH due to blending with a PVOH solution is not great enough to convert the sodium palmitate head group to the water insoluble free acid. Consequently, the contact angles remain high at all levels of complex incorporation.

As noted above, films cast from 100% amylose-hexadecylammonium chloride complexes were more wettable (lower contact angles) than those cast from 100% amylose-sodium palmitate complexes (Fanta et al. II, supra). This may be a result of the difference in the ionic charge of the head groups of the respective ligands. When a solution of the amylose-sodium palmitate complexes dries down, the amylose complexes separate from the amylopectin component (that was originally present in the high amylose starch used to prepare the inclusion complex) to form relatively hydrophobic aggregates (Fanta et al. II, supra). Such phase separation has been demonstrated with both synthetic mixtures of amylose and amylopectin solutions and with dissolved starch granules and was attributed to incompatibility between the two starch structures (German et al., Carbohydr. Polymers, (1992) 18:27; Kalichevsky & Ring, Carbohydr. Res., (1987) 62:323). Moreover, when this phase separation occurred, it was observed that the amylose-rich phase was above the amylopectin-rich phase. This phenomenon is consistent with the high contact angles observed at a wide range of PVOH: amylose-sodium palmitate complex ratios on the upper surface of the films. However, when the complexes have a cationic head group, as with the ammonium salt complexes, the ionic interactions that take place in solution between the head groups and both amylose and amylopectin may interfere with the mobility of the starch during drying, resulting in a more random, diffuse distribution of the amylose complexes and amylopectin. If we assume that amylopectin is more hydrophilic than the ammonium salt complex, this explanation is consistent with the observation of lower contact angles with the cationic ammonium salt complex than with the anionic carboxylic acid salt complex, as well as the lack of phase separation in films prepared from the cationic complexes.

Example 4

Antimicrobial Testing of Amylose/Carbohydrate Inclusion Complexes in Solution

Amylose Inclusion Complex Production

Inclusion complexes can be made as described above, or as described in this example. The inclusion complexes utilized in these tests were made in one of two methods—steam jet cooking (Fanta et al. I, supra) or microwave (Felker et al., Starch, (2013), 65, 864-874). Both of these references are herein specifically incorporated by reference in their entirety. Both of these methods have been shown produce amylose inclusion complexes. The steam jet cooking approach can make larger quantities of material (ex. 50 gram minimum), while the microwave approach can make as little as one gram of material. High amylose corn starch was utilized (Amylomaize VII, 70% amylose) and obtained from Cargill, Minneapolis, Minn.

Steam Jet Cooking Production of Sodium Palmitate Amylose Inclusion Complex

A dispersion of 110.4 g of high amylose starch in 1800 mL of deionized water was passed through a Penick & Ford (Penford Corp., Englewood, Colo.) laboratory model steam jet cooker operating under excess steam conditions. The temperature in the hydroheater was 140° C., the steam back pressure was 380 kPa (40 psig), and the steam line pressure from the boiler was 550 kPa (65 psig). Pumping rate through the jet-cooker was 1 L/min. The hot, jet cooked starch solution was collected in a 4 L stainless steel Waring blending container (Waring Products division, New Hartford, Conn.). Water solutions of palmitic acid sodium salt was prepared by dispersing 5.25 g of palmitic acid salt in 100 mL of water and then heating the dispersion to 90-95° C. This weight of palmitic acid salt is equal to 7.5% of the calculated weight of amylose in 110.4 g of high amylose starch. The hot solution of fatty acid salt was added to the hot starch dispersion in the blending container; and the dispersion was blended for 1 min. and then cooled in ice to 25° C. The sodium palmitate amylose inclusion complex was then isolated by freeze drying providing a yield of approximately 98%.

Steam Jet Production of N-hexadecylammonium Chloride Amylose Inclusion Complex

A dispersion of 110.4 g of high amylose starch (~9.4% moisture) in 1800 mL of deionized water was passed through a Penick & Ford (Penford Corp., Englewood, Colo.) laboratory model steam jet cooker operating under excess steam conditions (hydroheater temperature 140° C., steam back pressure 380 kPa (40 psig), steam line pressure 550 kPa (65 psig), and pumping rate 1 L/min). Solutions of the HCl salt of N-hexadecylamine was prepared by dispersing 5.25 g of N-hexadecylamine in 100 mL of solution with an HCl concentration equal to that required to convert the amine to its ammonium salt. This mass of N-hexadecylamine was equal to 7.5% of the weight of amylose (dry basis) in 110.4 g of high amylose corn starch. The acidified amine dispersions were then heated to 90° C. to obtain clear solutions. The hot solutions of fatty ammonium salts were then added to the hot starch dispersions, and the dispersions were blended for 1 min and then cooled in ice water to 25° C. The amylose-N-hexadecylammonium salt complex was then isolated by freeze-drying providing a yield of approximately 97%.

Microwave Production of N-hexadecylammonium Chloride Amylose Inclusion Complex

To 2.92 gr of high amylose corn starch was added 91.8 gr pf deionized water, 0.137 gr of N-hexadecylamine and 0.55 gr of 1.035 M HCl. The amount of N-hexadecylamine represents ~7.5% of the amylose in the starch used. The amount of HCl used is approximately an equal molar amount relative to the amine used. The mixture was subjected to microwave heating and isolated using freeze drying in the fashion described herein. The yield of product obtained after centrifuging and freeze drying was 98%.

Production of N-tetradecylammonium Chloride Amylose Inclusion Complex

To 2.97 gr of high amylose corn starch was added 96.8 gr pf deionized water, 0.135 gr of N-tetradecylamine and 0.63 gr of 1.035 M HCl. The amount of N-tetradecylamine represents ~7.5% of the amylose in the starch used. The amount of HCl used is approximately an equal molar amount relative to the amine used. The mixture was subjected to microwave heating and isolated using freeze drying in the fashion described herein. The yield of product obtained after centrifuging and freeze drying was 98%.

Production of N,N-dioctylammonium Chloride Amylose Inclusion Complex

To 2.93 gr of high amylose corn starch was added 96.8 gr pf deionized water, 0.137 gr of N,N-dioctylamine and 0.55 gr of 1.035 M HCl. The amount of N,N-dioctylamine represents ~7.5% of the amylose in the starch used. The amount of HCl used is approximately an equal molar amount relative to the amine used. The mixture was subjected to microwave heating and isolated using freeze drying in the fashion described herein. The yield of product obtained after centrifuging and freeze drying was 93%.

Production of N-dodecylanilium Chloride Amylose Inclusion Complex

To 2.94 gr of high amylose corn starch was added 97.4 gr pf deionized water, 0.143 gr of N-dodecylaniline and 0.51 gr of 1.035 M HCl. The amount of N-dodecylaniline represents ~7.5% of the amylose in the starch used. The amount of HCl used is approximately an equal molar amount relative to the amine used. The mixture was subjected to microwave heating and isolated using freeze drying in the fashion described herein. The yield of product obtained after centrifuging and freeze drying was 78%.

Production of N-methyl-N-octadecylammonium Chloride Amylose Inclusion Complex To 2.97 gr of high amylose corn starch was added 96.9 gr pf deionized water, 0.139 gr of N-methyl-N-octadecylamine and 0.47 gr of 1.035 M HCl. The amount of N-methyl-N-octadecylamine (a secondary amine) represents ~7.5% of the amylose in the starch used. The amount of HCl used is approximately an equal molar amount relative to the amine used. The mixture was subjected to microwave heating and isolated using freeze drying in the fashion described herein. The yield of product obtained after centrifuging and freeze drying was 99%.

Production of N,N-dimethyl-N-hexadecylammonium Chloride Amylose Inclusion Complex To 2.92 gr of high amylose corn starch was added 96.9 gr pf deionized water, 0.137 gr of N,N-dimethyl-N-hexadecylamine and 0.50 gr of 1.035 M HCl. The amount of N,N-dimethyl-N-hexadecylamine represents ~7.5% of the amylose in the starch used. The amount of HCl used is approximately an equal molar amount relative to the amine used. The mixture was subjected to microwave heating and isolated using freeze drying in the fashion described herein. The yield of product obtained after centrifuging and freeze drying was 99%.

Production of N-stearyl-N,N-diethanolammonium Chloride Amylose Inclusion Complex To 2.92 gr of high amylose corn starch was added 97.1 gr pf deionized water, 0.136 gr of N-stearyl-N,N-diethanolamine and 0.37 gr of 1.035 M HCl. The amount of N-stearyl-N,N-diethanolamine represents ~7.5% of the amylose in the starch used. The amount of HCl used is approximately an equal molar amount relative to the amine used. The mixture was subjected to microwave heating and isolated using freeze drying in the fashion described herein. The yield of product obtained after centrifuging and freeze drying was 99%.

Production of N-benzyl-N,N-dimethyl-N-hexadecylammonium Chloride Amylose Inclusion Complex To 2.91 gr of high amylose corn starch was added 97.1 gr pf deionized water, 0.143 gr of N-benzyl-N,N-dimethyl-N-hexadecylammonium chloride. The amount of N-benzyl-N,N-dimethyl-N-hexadecylammonium chloride represents ~7.5% of the amylose in the starch used. The mixture was subjected to microwave heating and isolated using freeze drying in the fashion described herein. The yield of product obtained after centrifuging and freeze drying was 99%.

Production of N,N,N-trimethyl-N-tetradecyl Ammonium Chloride Amylose Inclusion Complex To 3.06 gr of high amylose corn starch was added 97.4 gr pf deionized water, 0.137 gr of N,N,N-trimethyl-N-tetradecyl ammonium chloride. The amount of N,N,N-trimethyl-N-tetradecyl ammonium chloride (represents ~7.5% of the amylose in the starch used. The mixture was subjected to microwave heating and isolated using freeze drying in the fashion described herein. The yield of product obtained after centrifuging and freeze drying was 98%.

Production of N-hexadecyl-N,N,N-trimethyl Ammonium Bromide (CTAB) Amylose Inclusion Complex To 2.91 gr of high amylose corn starch was added 97.4 gr pf deionized water, 0.142 gr of N-hexadecyl-N,N,N-trimethyl ammonium bromide. The amount of N-hexadecyl-N,N,N-trimethyl ammonium bromide represents ~7.5% of the amylose in the starch used. The mixture was subjected to microwave heating and isolated using freeze drying in the fashion described herein. The yield of product obtained after centrifuging and freeze drying was 98%.

Production of Benzethonium Chloride Amylose Inclusion Complex

To 2.96 gr of high amylose corn starch was added 97.4 gr pf deionized water, 0.137 gr of benzethonium chloride (a known antimicrobial). The amount of benzethonium chloride represents ~7.5% of the amylose in the starch used. The mixture was subjected to microwave heating and isolated using freeze drying in the fashion described herein. The yield of product obtained after centrifuging and freeze drying was 72%.

Production of N-hexadecylpyridinium Chloride Amylose Inclusion Complex

To 2.93 gr of high amylose corn starch was added 97.7 gr pf deionized water, 0.139 gr of N-hexadecylpyridinium chloride. The amount of N-hexadecylpyridinium chloride represents ~7.5% of the amylose in the starch used. The mixture was subjected to microwave heating and isolated using freeze drying in the fashion described herein. The yield of product obtained after centrifuging and freeze drying was 99%.

Production of N-lauroylcholine Chloride Amylose Inclusion Complex

To 2.93 gr of high amylose corn starch was added 97.8 gr pf deionized water, 0.141 gr of N-lauroylcholine chloride. The amount of N-lauroylcholine chloride represents ~7.5% of the amylose in the starch used. The mixture was subjected to microwave heating and isolated using freeze drying in the fashion described herein. The yield of product obtained after centrifuging and freeze drying was 96%.

Production of N,N-dimethyl-N,N-dipalmitylammonium Bromide Inclusion Complex

To 2.99 gr of high amylose corn starch was added 97.4 gr pf deionized water, and 0.147 gr of N,N-dimethyl-N,N- dipalmitylammonium bromide. The amount of N,N-dimethyl-N,N-dipalmitylammonium bromide represents ~7.5% of the amylose in the starch used. The mixture was subjected to microwave heating and isolated using freeze drying in the fashion described herein. The yield of product obtained after centrifuging and freeze drying was 99%.

Production of N,N-Dimethyl-N-octadecyl N-[3-(trimethyloxysilyl)propyl] Ammonium Chloride Inclusion Complex To 2.96 gr of high amylose corn starch was added 97.4 gr pf deionized water, and 0.326 gr of N,N-dimethyl-N-octadecyl N-[3-(trimethyloxysilyl)propyl] ammonium chloride (42% solids). The amount of N,N-dimethyl-N-octadecyl N-[3-(trimethyloxysilyl)propyl] ammonium chloride (a known antimicrobial) represents ~7.5% of the amylose in the starch used. The mixture was subjected to microwave heating and isolated using freeze drying in the fashion described herein. The yield of product obtained after centrifuging and freeze drying was 99%.

Production of Variant N-hexadecylammonium Chloride Inclusion Complexes

In order to test the effects of different concentrations of amine in inclusion complexes on antimicrobial activity, several concentrations of N-hexadecylammonium chloride were prepared, as was an inclusion complex using dextrin instead of amylose. Additionally, a variant inclusion complex formed using 25% amylose starch (instead of the 70% amylose used for other preparations) and Nhexadecylamine (90% purity) was tested.

For 3.0%, 9%, and 15% N-hexadecylammonium chloride complex formation, the microwave heating and freeze-drying protocol described herein were utilized. For the 3.0% preparation, 3.03 gr of high amylose corn starch was added 96.8 gr pf deionized water, 0.057 gr of N-hexadecylamine and 0.22 gr of 1.035 M HCl. The yield of product obtained after centrifuging and freeze drying was 98%. For the 9.0% preparation, 2.95 gr of high amylose corn starch was added 96.7 gr pf deionized water, 0.168 gr of N-hexadecylamine and 0.67 gr of 1.035 M HCl. The yield of product obtained after centrifuging and freeze drying was 99%. For the 15% preparation, 2.93 gr of high amylose corn starch was added 96.9 gr of deionized water, 0.275 gr of N-hexadecylamine and 1.11 gr of 1.035 M HCl. The amount of HCl used is approximately an equal molar amount relative to the amine used. The yield of product obtained after centrifuging and freeze drying was 99%.

For the 25% amylose inclusion complex production, a dispersion of 110.4 g of high amylose starch (~9.4% moisture) in 1800 mL of deionized water was passed through a Penick & Ford (Penford Corp., Englewood, Colo.) laboratory model steam jet cooker operating under excess steam conditions (hydroheater temperature 140° C., steam back pressure 380 kPa (40 psig), steam line pressure 550 kPa (65 psig), and pumping rate 1 L/min). Solutions of the HCl salt of N-hexadecylamine (90% purity) was prepared by dispersing 1.88 g of N-hexadecylamine (90% purity) in 100 mL of solution with an HCl concentration equal to that required to convert the amine to its ammonium salt. This mass of N-hexadecylamine was equal to 7.5% of the weight of amylose (dry basis—note 25% amylose versus earlier examples of ~70%) in 110.4 g of high amylose corn starch. The acidified amine dispersions were then heated to 90° C. to obtain clear solutions. The hot solutions of fatty ammonium salts were then added to the hot starch dispersions, and the dispersions were blended for 1 min and then cooled in ice water to 25° C. The amylose-N-hexadecylammonium salt complex was then isolated by spray-drying providing a yield of approximately 97%.

For the N-hexadecylammonium chloride-dextrin inclusion complex, 3.02 gr of dextrin was added 96.7 gr pf deionized water, 0.149 gr of N-hexadecylamine and 0.55 gr of 1.035 M HCl. The mixture was subjected to microwave heating and isolated using freeze drying in the fashion described herein. The yield of product obtained after centrifuging and freeze drying was 99%.

Production of N-Octadecylammonium Chloride Inclusion Complex

To 2.92 gr of high amylose corn starch was added 96.5 gr of deionized water, 0.139 gr of N-octadecylamine and 0.50 gr of 1.035 M HCl. The amount of N-octadecylamine represents ~7.5% of the amylose in the starch used. The amount of HCl used is approximately an equal molar amount relative to the amine used. The mixture was subjected to microwave heating and isolated using freeze drying in the fashion described above. The yield of product obtained after centrifuging and freeze drying was 99%.

Production of N-dodecylammonium Chloride Inclusion Complex

To 2.92 gr of high amylose corn starch was added 96.8 gr of deionized water, 0.139 gr of N-dodecylamine and 0.73 gr of 1.035 M HCl. The amount of N-dodecylamine represents ~7.5% of the amylose in the starch used. The amount of HCl used is approximately an equal molar amount relative to the amine used. The mixture was subjected to microwave heating and isolated using freeze drying in the fashion described above. The yield of product obtained after centrifuging and freeze drying was 97%.

Production of N,N-didecyl-N-methylammonium Chloride Inclusion Complex

To 2.93 gr of high amylose corn starch was added 96.6 gr of deionized water, 0.14 gr of N,N-didecyl-N-methylamine and 0.43 gr of 1.035 M HCl. The amount of N,N-didecyl-N-methylamine represents ~7.5% of the amylose in the starch used. The amount of HCl used is approximately an equal molar amount relative to the amine used. The mixture was subjected to microwave heating and isolated using freeze drying in the fashion described above. The yield of product obtained after centrifuging and freeze drying was 99%.

Production of N,N-didodecylammonium Chloride Inclusion Complex

To 2.94 gr of high amylose corn starch was added 96.7 gr of deionized water, 0.138 gr of N,N-didodecylamine and 0.37 gr of 1.035 M HCl. The amount of N,N-didodecylamine represents ~7.5% of the amylose in the starch used. The amount of HCl used is approximately an equal molar amount relative to the amine used. The mixture was subjected to microwave heating and isolated using freeze drying in the fashion described above. The yield of product obtained after centrifuging and freeze drying was 99%.

Production of N,N,N-tri-(2-ethyl)hexylammonium Chloride Inclusion Complex

To 2.92 gr of high amylose corn starch was added 96.6 gr of deionized water, 0.135 gr of N,N,N-tri-(2-ethyl)hexylamine and 0.37 gr of 1.035 M HCl. The amount of N,N,N-tri-(2-ethyl)hexylamine represents ~7.5% of the amylose in the starch used. The amount of HCl used is approximately an equal molar amount relative to the amine used. The mixture was subjected to microwave heating and isolated using freeze drying in the fashion described above. The yield of product obtained after centrifuging and freeze drying was 99%.

Production of N-hexamethylammonium Chloride Complexes Using Other Polysaccharides To test the ability of inclusion complexes made with other polysaccharides to inhibit growth of microbes, inclusion complexes made from N-hexamethylammonium and waxy corn starch, dextrin 2, dextrin 3, potato starch, wheat starch, rice starch and tapioca starch were prepared using the microwave heating approach described herein.

For the waxy corn starch complexes, 2.92 gr of waxy corn starch was added to 96.5 gr pf deionized water, 0.138 gr of N-hexadecylamine and 0.55 gr of 1.035 M HCl. The yield of product obtained after centrifuging and freeze drying was 98%. For the dextrin 2 complexes, 2.83 gr of dextrin 2 was added to 93.8 gr pf deionized water, 0.137 gr of N-hexadecylamine and 0.57 gr of 1.035 M HCl. The yield of product obtained after centrifuging and freeze drying was 99%. For the dextrin 3 complexes, 2.77 gr of Dextrin 3 was added to 94.1 gr pf deionized water, 0.137 gr of N-hexadecylamine and 0.55 gr of 1.035 M HCl. The yield of product obtained after centrifuging and freeze drying was 99%. For the potato starch complexes, 2.63 gr of potato starch was added to 94.1 gr pf deionized water, 0.139 gr of N-hexadecylamine and 0.55 gr of 1.035 M HCl. The yield of product obtained after centrifuging and freeze drying was 98%. For the wheat starch complexes, 2.83 gr of wheat starch was added to 93.8 gr pf deionized water, 0.138 gr of N-hexadecylamine and 0.56 gr of 1.035 M HCl. The yield of product obtained after centrifuging and freeze drying was 99%. For the rice starch complexes, 2.83 gr of rice starch was added to 93.8 gr pf deionized water, 0.140 gr of N-hexadecylamine and 0.55 gr of 1.035 M HCl. The yield of product obtained after centrifuging and freeze drying was 98%. For the tapioca starch complexes, 2.95 gr of tapioca starch was added to 96.9 gr pf deionized water, 0.042 gr of N-hexadecylamine and 0.16 gr of 1.035 M HCl. The yield of product obtained after centrifuging and freeze drying was 99%.

Antimicrobial Testing

To define the ability of select amylose inclusion complexes to inhibit the growth of microbes, a panel of microorganisms was selected and tested against three different concentrations (0.04, 0.008, and 0.0016% (v/v)) of test compounds along with a blank RPMI-1640 as a sterility control and a 0% concentration of each test material against each isolate. The macro-broth dilution MICs for each fungal, yeast, or bacterial organism was performed following the CLSI standard M27-A3 as the guideline and measuring OD600 on a spectrophotometer.

Unless specified otherwise, test materials were autoclaved as 2% aqueous solutions. A 5-fold dilution of the test material was prepared in RPMI-1640 broth. Two additional 5-fold dilution series were prepared for the test materials in RPMI-1640. Stock test solutions of 0, 0.4, 0.08, and 0.016% were used for micro-assay to determine growth inhibition.

Microbial Isolates

The following organisms from ATCC and NRRL culture collections were tested for antimicrobial susceptibility: *Aureobasidium pullulans* ATCC 58559, *Staphylococcus aureus* ATCC 29213, *Erwinia amylovora* ATCC 58153, *Penicillium verruculosum* NRRL 1050, *Aspergillus niger* NRRL 3, *Streptococcus agalactiae* B-1815, *Pseudomonas aeruginosa* NRRL B-771, *Klebsiella oxytoca* NRRL B-59613, *Acinetobacter johnsonii* NRRL B-14921, *Cyberlindnera fabianii* NRRL Y-1872, *Debaryomyces fabryi* NRRLYB-499, *Rhodotorula mucilaginosa* NRRL Y-844, *Saccharomyces bayanus* NRRL Y-846, *Saccharomyces paradoxus* Y-147, *Candida parapsilosis* NRRL Y-182, *Candida glabrata* NRRL Y-1417, *Citeromyces matritensis* NRRL Y-1506, *Candida intermedia* NRRL Y10925, *Candida milleri* NRRL Y-7245, *Protohteca wickehamii* NRRL YB-4330, *Citeromyces matritensis* (NRRL Y-1506), *Ogataea polymorpha* NRRL Y-1798, *Candida aaseri* NRRL YB-4234, *Candida dubliniensis* NRRL Y-17841, *Trichosporon cutaneum* NRRL Y-1490, *Fellomyces fuzhouensis* NRRL Y-7956, *Candida tropicalis* NRRL Y-2001, *Kluyveromyces lactic* NRRL Y-8279, *Candida rugosa* NRRL YB-182, *Candida kefyr* ATCC 3135, *Yarrowia lipolytica* ATCC 9773, *Trichosporon dermatis* ATCC 204094, *Staphylococcus saprophyticus* subspecies *saprophyticus* NRRL B-14751, *Chryseobacterium indologenes* NRRL B-14848. Organisms were propagated individually on their recommended growth medium and at recommended temperature. All organisms were subcultured onto Sabouraud dextrose agar and grown 28° C. for 48 hours, except for *Clostridium acetobutylicum* NRRL B-527, which was grown under anaerobic conditions at 37° C. for 48 hours.

Fungal and bacterial inocula were prepared by picking five colonies about 1 mm in diameter and suspending into 5 mL of sterile 0.85% saline to produce a 0.5 McFarland standard, vortexed, measured using a Bectin Dickinson CrystalSpec Nephelometer, and adjusted if necessary. The fungal inocula were prepared by flooding hyphae on plate in 5 mL sterile 0.85% saline, vortexed, measured using CrystalSpec Nephalometer, and adjusted as necessary for a McFarland value of 0.5. A working suspension was prepared by diluting the stock solutions for each organism 100-fold into RPMI-1640 (RPMI-1640 medium supplemented with L-glutamine, 2% glucose, and buffered to pH 7.0 with 0.156 M 3-N-morpholinopropane-sulphonic acid (MOPS)).

Determination of Inhibitory Response

The ability of the test materials to inhibit microbial growth was determined using a broth micro-dilution assay (reference CLSI standard M27-A3). Testing was performed in 96 well flat-bottomed plates. Briefly, 20 µL of test solution was pipetted aseptically into designated triplicate wells of 96 well plates. Working suspension (180 µL) of each organism was added in triplicate to each concentration of each test material. Optical densities at 600 nm (OD600) were measured on a SpectraMax M2 plate reader (Molecular Devices) at 0 hr. The 96 well plates were incubated aerobically at 28° C. for 3 days; except *Clostridium acetobutylicum* NRRL B-527 was grown anaerobically at 37° C. for 3 days. After 64-hour incubation, OD600 was again measured on each plate to determine if the growth of the microbes was inhibited. Triplicate sterile control wells containing only RPMI-1640 broth for each test material and concentration was tested and remained optically clear. For certain tests, visual examination of the plates was made.

Results

The results of the antimicrobial tests of the various compounds are shown below in Table 2. Minimum inhibitory concentration (MIC) was determined as the lowest concentration of the test solution that resulted in lack of any turbidity. Where a value is not shown, then the range in percent reduction in observed growth (turbidity) at 0.04 is shown, unless otherwise specified (with >0.04 indicating no reduction in turbidity at any tested concentration).

TABLE 2

Antimicrobial effects of various inclusion complexes

| | MIC |
|---|---|
| Sodium palmitate - amylose | |
| A. pullulans | >0.04 (no activity) |
| P. verruculosum | >0.04 (no activity) |
| A. niger | >0.04 (no activity) |
| S. agalactiae | >0.04 (no activity) |
| S. aureus | >0.04 (no activity) |
| P. aeruginosa | >0.04 (no activity) |
| E. amylovora | >0.04 (no activity) |
| A. johnsonii | >0.04 (no activity) |
| N-Tetradecylammonium chloride - amylose | |
| A. pullulans | 0.008 |
| P. verruculosum | 0.008 |
| A. niger | 0.008 |
| S. agalactiae | 0.008 |
| S. aureus | 0.008 |
| P. aeruginosa | 25-49% |
| E. amylovora | 25-49% |
| A. johnsonii | 25-49% |
| N-Hexadecylammonium chloride (7.5%) - amylose (Steam jet) | |
| Candida aaseri | <0.0008 |
| C. dubliniensis | 0.004 |
| C. glabrata | ≤0.02 |
| C. intermedia | ≤0.02 |
| C. kefyr | 0.004 |
| C. milleri | ≤0.02 |
| C. parapsilosis | ≤0.02 |
| C. rugosa | 0.004 |
| C. tropicalis | 0.02 |
| Citeromyces matritensis | 0.004 |
| Cyberlindnera fabianii | ≤0.02 |
| Debaryomyces fabryi | ≤0.02 |
| Fellomyces fuzhouensis | <0.0008 |
| Kluyveromyces lactis | 0.004 |
| Ogataea polymorpha | 0.004 |
| Rhodotorula mucilaginosa | ≤0.02 |
| Saccharomyces bayanus | ≤0.02 |
| S. paradoxus | ≤0.02 |
| Trichosporon cutaneum | 0.004 |
| T. dermatis | 0.02 |
| Yarrowia lipolitica | 0.004 |
| Chryseobacterium indologenes | 25-49%, >0.02 |
| Staphylococcus saprophyticus saprophyticus | 0.0008 |
| Prototheca wickehamii | 0.004 |
| N-Hexadecylammonium chloride (7.5%) - amylose (microwave) | |
| A. pullulans | 0.008 |
| P. verruculosum | 0.008 |
| A. niger | 0.04 |
| S. aureus | 0.008 |
| N,N-Dioctylammonium chloride - amylose | |
| A. pullulans | 0.008 |
| P. verruculosum | 0.008 |
| A. niger | 0.04 |
| S. agalactiae | 0.04 |
| S. aureus | 0.04 |
| E. coli | >0.04 (no activity) |
| P. aeruginosa | 25-49% |
| E. amylovora | 25-49% |
| K. oxytoca | >0.04 (no activity) |
| A. johnsonii | 50-95% |
| N-Dodecylanilium chloride - amylose | |
| P. verruculosum | 25-49% |
| S. aureus | 25-49% |
| N-Methyl-N-octadecylammonium chloride - amylose | |
| A. pullulans | 50-95% |
| P. verruculosum | 50-95% |
| S. aureus | 0.008 |
| N,N-Dimethyl-N-hexadecylammonium chloride - amylose | |
| A. pullulans | 50-95% |
| P. verruculosum | 0.04 |
| A. niger | 25-49% |
| S. agalactiae | 50-95% |
| N-Stearyl-N,N-diethanolammonium chloride - amylose | |
| A. pullulans | >0.04 (no activity) |
| P. verruculosum | >0.04 (no activity) |
| A. niger | >0.04 (no activity) |
| S. aureus | >0.04 (no activity) |
| E. coli | >0.04 (no activity) |
| P. aeruginosa | >0.04 (no activity) |
| E. amylovora | >0.04 (no activity) |
| K. oxytoca | >0.04 (no activity) |
| A. johnsonii | >0.04 (no activity) |
| N-Hexadecyl-N,N,N-trimethylammonium bromide - amylose | |
| A. pullulans | 50-95% |
| P. verruculosum | 0.04 |
| S. agalactiae | 0.008 |
| S. aureus | 0.008 |
| Benzethonium chloride - amylose | |
| A. pullulans | 0.008 |
| P. verruculosum | 0.0016 |
| S. agalactiae | 0.04 |
| S. aureus | 0.04 |
| A. johnsonii | 0.04 |
| Benzethonium chloride - amylose | |
| S. aureus | 25-49% |
| N-Hexadecylpyridinium chloride - amylose | |
| A. pullulans | 50-95% |
| P. verruculosum | 0.008 |
| S. agalactiae | 25-49% |
| S. aureus | 0.0016 |
| N-Lauroylcholine chloride | |
| A. pullulans | 50-95% |
| P. verruculosum | 50-95% |
| S. agalactiae | 25-49% |
| S. aureus | 50-95% |
| N,N-Dimethyl-N,N-dipalmitylammonium chloride - amylose | |
| A. pullulans | >0.04 (no activity) |
| P. verruculosum | >0.04 (no activity) |
| A. niger | >0.04 (no activity) |
| S. aureus | >0.04 (no activity) |
| E. coli | >0.04 (no activity) |
| P. aeruginosa | >0.04 (no activity) |
| E. amylovora | >0.04 (no activity) |
| K. oxytoca | >0.04 (no activity) |
| A. johnsonii | >0.04 (no activity) |

TABLE 2-continued

Antimicrobial effects of various inclusion complexes

| | MIC |
|---|---|
| N,N-Dimethyl-N-octadecyl N-[3-(trimethyloxysilyl)propyl]ammonium chloride - amylose | |
| S. aureus | 25-49% |
| N-Hexadecylammonium chloride (3%) - amylose | |
| A. pullulans | 50-95% |
| P. verruculosum | 25-49% |
| A. niger | 50-95% |
| N-Hexadecylammonium chloride (9%) - amylose | |
| A. pullulans | 0.008 |
| P. verruculosum | 0.008 |
| A. niger | 0.04 |
| S. agalactiae | 0.008 |
| S. aureus | 0.04 |
| A. johnsonii | 25-49% |
| N-Hexadecylammonium chloride (15%) - amylose | |
| A. pullulans | 0.0016 |
| P. verruculosum | 0.0016 |
| A. niger | 0.04 |
| S. agalactiae | 0.0016 |
| S. aureus | 0.0016 |
| E. coli | 25-49% |
| A. johnsonii | 0.008 |
| N-Hexadecylammonium chloride (7.5%) - dextrin | |
| A. pullulans | 0.008 |
| P. verruculosum | 0.008 |
| A. niger | 0.008 |
| S. agalactiae | 0.008 |
| S. aureus | 0.008 |
| E. amylovora | 25-49% |
| A. johnsonii | 0.04 |
| N-Hexadecylammonium chloride (7.5%-90% purity) - amylose (25%) | |
| A. pullulans | No visual growth |
| S. aureus | Visual growth |
| E. amylovora | Visual growth |
| N-Octadecylammonium chloride | |
| A. pullulans | 25-49% |
| P. verruculosum | 25-49% |
| S. aureus | 0.04 |
| N-Dodecylammonium chloride | |
| A. pullulans | 0.008 |
| P. verruculosum | 0.0016 |
| A. niger | 0.008 |
| S. agalactiae | 0.04 |
| S. aureus | 0.04 |
| E. coli | 0.04 |
| E. amylovora | 0.04 |
| A. johnsonii | 0.04 |
| N,N-Didecyl-N-methylammonium chloride | |
| P. verruculosum | 0.04 |
| S. agalactiae | 0.04 |
| N,N-didodecylammonium chloride - amylose | |
| A. pullulans | >0.04 (no activity) |
| P. verruculosum | >0.04 (no activity) |
| A. niger | >0.04 (no activity) |
| S. agalactiae | >0.04 (no activity) |
| S. aureus | >0.04 (no activity) |
| E. coli | >0.04 (no activity) |
| P. aeruginosa | >0.04 (no activity) |
| E. amylovora | >0.04 (no activity) |
| K. oxytoca | >0.04 (no activity) |
| A. johnsonii | >0.04 (no activity) |
| N,N,N-tri-(2-ethyl)hexylammonium chloride - amylose | |
| A. pullulans | >0.04 (no activity) |
| P. verruculosum | >0.04 (no activity) |
| A. niger | >0.04 (no activity) |
| S. agalactiae | >0.04 (no activity) |
| S. aureus | >0.04 (no activity) |
| E. coli | >0.04 (no activity) |
| P. aeruginosa | >0.04 (no activity) |
| E. amylovora | >0.04 (no activity) |
| K. oxytoca | >0.04 (no activity) |
| A. johnsonii | >0.04 (no activity) |
| N-Hexadecylammonium chloride (7.5%) - waxy corn starch | |
| A. pullulans | 0.0016 |
| P. verruculosum | 0.008 |
| A. niger | 0.04 |
| S. agalactiae | 0.0016 |
| S. aureus | 0.0016 |
| A. johnsonii | 0.04 |
| N-Hexadecylammonium chloride (7.5%) - dextrin 2 | |
| A. pullulans | 0.0016 |
| P. verruculosum | 0.0016 |
| A. niger | 0.04 |
| S. agalactiae | 0.0016 |
| S. aureus | 0.008 |
| E. coli | 50-95% |
| A. johnsonii | 0.04 |
| N-Hexadecylammonium chloride (7.5%) - dextrin 3 | |
| A. pullulans | 0.0016 |
| P. verruculosum | 0.0016 |
| A. niger | 0.04 |
| S. aureus | 0.008 |
| E. coli | 0.04 |
| A. johnsonii | 0.04 |
| N-Hexadecylammonium chloride (7.5%) - potato starch | |
| A. pullulans | 0.008 |
| P. verruculosum | 0.0016 |
| A. niger | 0.008 |
| S. aureus | 0.008 |
| E. coli | 25-49% |
| A. johnsonii | 0.008 |
| N-Hexadecylammonium chloride (7.5%) - wheat starch | |
| A. pullulans | 0.0016 |
| P. verruculosum | 0.0016 |
| A. niger | 0.04 |
| S. aureus | 0.008 |
| E. coli | 50-95% |
| A. johnsonii | 0.008 |
| N-Hexadecylammonium chloride (7.5%) - rice starch | |
| A. pullulans | 0.008 |
| P. verruculosum | 0.0016 |
| A. niger | 0.04 |
| S. aureus | 0.008 |
| A. johnsonii | 0.04 |
| N-Hexadecylammonium chloride (7.5%) - tapioca starch | |
| A. pullulans | 25-49% |
| P. verruculosum | 0.04 |
| S. agalactiae | 0.04 |

Example 5

Analysis of Polymeric Films Having Various Plasticizers Containing Hex-Am-Amylose Inclusion Complexes In order to define the ability of polymeric films containing N-hexadecylammonium chloride amylose inclusion complexes to inhibit the growth of microbes, a panel of 3 microorganisms were selected and tested against polyvinyl alcohol (133,000 m.w., 99% hydrolyzed) having six different plasticizers at 20% loading.

Test materials were autoclaved as 1% or 4% aqueous solutions. In all examples, N-hexadecylammonium chloride amylose inclusion complex was used as the agent. The amount of N-hexadecylammonium chloride present in the starch sample was 7.5% of the amylose present in the ~70% amylose starch material.

For preparation of the blends, the N-hexadecylammonium chloride amylose inclusion complex was dispersed in water to give a 1% solution, or a 4% solution only for the polyvinyl alcohol blend. This was heated to 80° C., on reaching 80° C., the now clear solution was cooled quickly to room temperature by cooling in an ice bath. For each of the desired polymer blends, the other polymer of interest was prepared as a 1% solution in water (except for casein which was dissolved in pH=2 water, and polyvinyl alcohol which was prepared as a 4% solution). The polymers were dissolved using standard conditions, if they were not soluble at room temperature, they were heated to 80° C. Two polymer blends were prepared, 1part N-hexadecylammonium chloride amylose inclusion complex and 1part polymer, or 2 parts N-hexadecylammonium chloride amylose inclusion complex and 1part polymer. For both of these blends, 150 µL of the polymer blend solution (75 µl for the polyvinyl alcohol blend) was pipetted aseptically into designated triplicate wells of 96 well plates and allowed to dry for 72 h.

Antimicrobial Testing

The following representative organisms from ATCC culture collections were tested for antimicrobial susceptibility: *Aureobasidium pullulans* ATCC 58559, *Staphylococcus aureus* ATCC 29213, and *Erwinia amylovora* ATCC 58153. Organisms were propagated individually on their recommended growth medium and at recommended temperature. All organisms were subcultured onto Sabouraud dextrose agar and grown 28° C. for 48 hours.

Yeast and bacterial inocula were prepared by picking five colonies about 1 mm in diameter and suspending into 5 mL of sterile 0.85% saline to produce a 0.5 McFarland standard, vortexed, measured using a Bectin Dickinson CrystalSpec Nephelometer, and adjusted if necessary. A working suspension was prepared by diluting the stock solutions for each organism 100-fold into RPMI-1640 (RPMI-1640 medium supplemented with L-glutamine, 2% glucose, and buffered to pH 7.0 with 0.156 M 3-N-morpholinopropane-sulphonic acid (MOPS)).

The ability of the polymeric films containing N-hexadecylammonium chloride amylose inclusion complex (Hex-Am) test materials to inhibit microbial growth was determined using a broth micro-dilution assay (reference CLSI standard M27-A3). Testing was performed in 96 well flat-bottomed plates. Briefly, to each well prepared with a film, a working suspension (180 µL) of each organism was added in triplicate to each polymer blended film of each test material. The 96 well plates were incubated aerobically at 28° C. for 3 days; except after 64-hour incubation, samples of the media were removed and plated and then allowed to grow for 72 hours at 28° C. to assess if microbial growth occurred. Plates (72 hr) were scored and compared visually with the amount of growth in the growth control wells (no test material) for each organism where turbidity is an indication of microbial growth. For both OD600 measurements and visually scoring analysis methods, the MIC is the lowest concentration of test material that prevents visible growth of a given organism when compared to growth control wells containing 0% test material for each organism. Triplicate sterile control wells containing only RPMI-1640 broth for each test material and concentration was tested and remained optically clear. Results are shown in Table 3 ("+" signifies no visual microbial growth after 72 hours; "0" signifies visual growth after 72 hours) and demonstrate that the presence of plasticizers has no effect on the antimicrobial characteristics of Hex-Am-PVOH films.

TABLE 3

Antimicrobial activity of plasticizer-containing complexes

| Plasticizer | Treatment | Ratio | A. pullulans | S. aureus |
| --- | --- | --- | --- | --- |
| No treatment | | | 0 | 0 |
| HexAm with no plasticizer | | | + | + |
| Glycerol | 4% | 1:2 poly:HexAm | + | + |
| Sorbitol | 4% | 1:2 poly:HexAm | + | + |
| Lactic acid | 4% | 1:2 poly:HexAm | + | + |
| Polyethylene glycol, 200 m.w. | 4% | 1:2 poly:HexAm | + | + |
| Ethyl lactate | 4% | 1:2 poly:HexAm | + | + |
| Salicylic acid | 4% | 1:2 poly:HexAm | + | + |
| Locust bean gum | 1% | 1:1 poly:HexAm | + | + |
| Locust bean gum | 1% | 1:2 poly:HexAm | + | 0 |
| Guar gum | 1% | 1:1 poly:HexAm | + | + |
| Guar gum | 1% | 1:2 poly:HexAm | + | + |
| Cationic starch | 1% | 1:2 poly:HexAm | + | + |
| Soluble starch | 1% | 1:2 poly:HexAm | + | + |
| Polyethylene oxide 100,000 m.w. | 1% | 1:2 poly:HexAm | + | + |
| Polyvinyl pyrolidone 55,000 m.w. | 1% | 1:1 poly:HexAm | + | + |
| Polyvinyl pyrolidone 55,000 m.w. | 1% | 1:2 poly:HexAm | + | + |
| Polyacrylamide 1000,000 m.w. | 1% | 1:1 poly:HexAm | + | + |
| Polyacrylamide 1000,000 m.w. | 1% | 1:2 poly:HexAm | + | + |
| Hydroxymethylpropyl cellulose | 1% | 1:1 poly:HexAm | + | 0 |
| Hydroxymethylpropyl cellulose | 1% | 1:2 poly:HexAm | + | + |
| Hydroxypropyl cellulose | 1% | 1:1 poly:HexAm | + | + |
| Hydroxypropyl cellulose | 1% | 1:2 poly:HexAm | + | + |
| Carboxymethyl cellulose | 1% | 1:2 poly:HexAm | + | 0 |

TABLE 3-continued

Antimicrobial activity of plasticizer-containing complexes

| Plasticizer | Treatment | Ratio | A. pullulans | S. aureus |
|---|---|---|---|---|
| Polyvinyl alcohol 133,000 m.w. 99% hydrolyzed | 4% | 1:1 poly:HexAm | + | + |
| Casein | 1% | 1:1 poly:HexAm | 0 | + |

Example 6

Protection Against Wood Rot Fungus

To examine one practical usage of the compounds of the present invention, vacuum impregnated wood cubes were tested for resistance to wood-rot fungi using Standard Method of Testing Wood Preservatives by Laboratory Soil-Block Cultures E10-06 (American Wood Protection Association Standards. 2012. Standard method of testing wood preservatives by laboratory soil block cultures, E10-12, In: Annual Book of AWPA Standards, Birmingham, Ala., USA, pp. 327-335). White-rot fungi (*Trametes versicolor* (L. Fr.) Pil. (MAD 697) was tested on Yellow Poplar (YP) cubes. The 1-cm$^3$ wood cubes were conditioned to a constant mass at 27° C. and 70% relative humidity (RH) and weighed prior to vacuum impregnation using a 2% Hex-Am/2% PVOH water solution. After impregnation, the solvent was allowed to evaporate and the blocks re-conditioned to a constant mass at 27° C. and 70% RH. The % mass loss was determined after an 8-week exposure to the fungi at 27° C. and 70% RH. There were six replications of each treatment. Results show that wood impregnated with the antimicrobial compositions described herein are resistant to wood rot, decreasing wood mass loss by half.

TABLE 4

Protection against wood mass loss in Hex-Am/PVOH treated wood

| Sample | Mean mass loss (%) | Mass loss (%), st. dev. |
|---|---|---|
| Untreated (water control) | 61.5 | 1.5 |
| Hex-Am/PVOH | 30.0 | 11.0 |

Example 7

Protection of Potatoes Against Dry Rot Disease with Hex-Am and Hex-Am/PVOH

Figure 6:
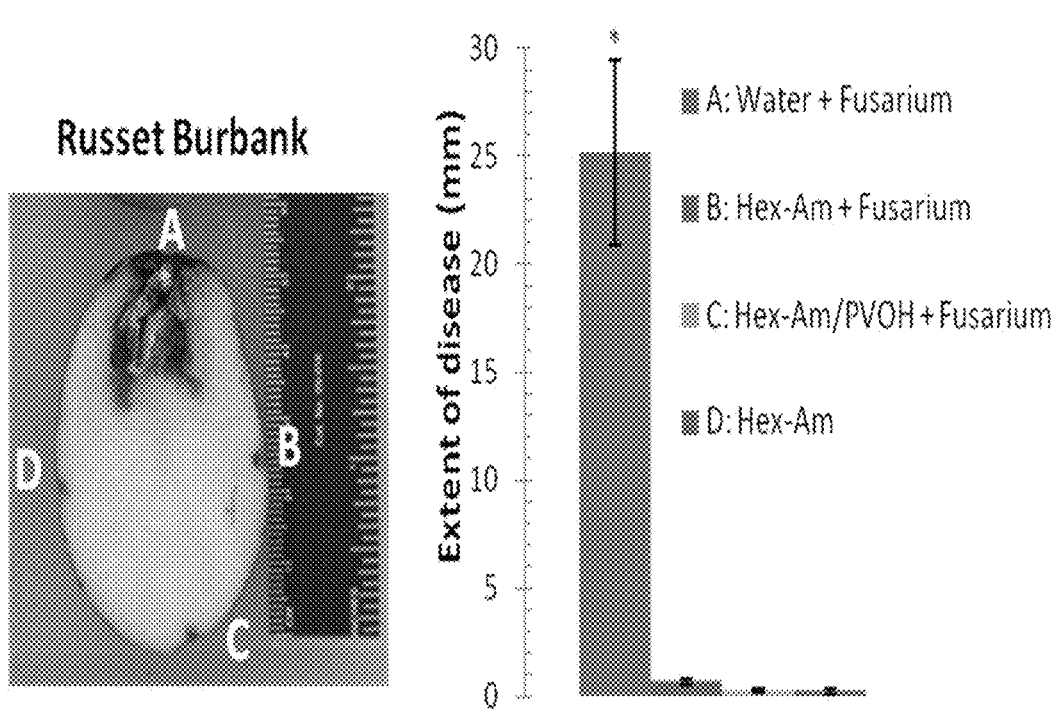
FIG. 6 provides pictorial representation of a sample experimental infected potato and the ability of Hex-Am and Hex-Am/PVOH to protect against dry rot. Also shown is a graphic representation of the extent of disease prevention.

In Situ Test of Hex-Am on Dry Rot Disease Development on 5 Varieties of Potatoes Under Storage Conditions Hex-Am was produced as described herein at a concentration of 3% solids. Conidia of *Fusarium sambucinum* R-6380 were produced and set to a concentration of 5×10$^3$ conidia/mL. Treatment suspensions consisted of conidia of *F. sambucinum* mixed 50:50 with Hex-Am or water (as control). Treatments suspensions were used to inoculate 5 different varieties of potatoes (Superior, Russet Norkotah, Russet Burbank, Yukon gold, and Red Norland). Potatoes were wounded with a 2 mm diameter×2 mm length steel pin. Wounds were then inoculated with 5 μL of the treatment suspension. For each potato variety, each treatment was repeated on twenty-four size B, washed seed potatoes (Wisconsin Seed Potato Certification Program, University of Wisconsin Madison, Antigo, Wis.). Prior to washing, tubers were kept in a cold room at 4° C. and then allowed to acclimate to ~25° C. for 24 h before initiating a bioassay. Each potato received each treatment. Each potato then was placed in a plastic weigh boat containing a dry 2.5 cm square of Wypall paper towel. Boats were moved to trays, the potatoes covered with two dry paper towels, and trays placed in plastic bags. Two additional towels that were moistened with 40 mL of water each then were placed on either side of the tray, the bags tightly sealed, and then stored for 21 days at 15° C. Dry rot then was evaluated by slicing lengthwise through the center of each of the wounds. The extent of disease in each wound was rated by adding the greatest depth and width measurements (mm) of discolored necrotic tissue extending below and to the sides of the wound. The experiment was conducted twice and data from a representative experiment are presented in Table 5. For data obtained for each potato variety, statistical differences were determined using an analysis of variance, and after obtaining a significant F test statistic, the treatment means were separated by the Tukey adjusted least significant difference (Proc mixed SAS 9.4), α=0.05, n=24. For the data presented in Table 5, RB-Russet Burbank, Reds-Red Norland, Sup-Superior, YG-Yukon gold, and RN-Russet Norkotah. The extent of disease implies mm of damage for each item. Within each potato variety, items with differing letters are statistically different. An exemplary test potato and results are shown in FIG. 6.

TABLE 5

Protection against dry rot by Hex-Am treatment

| Potato variety | Treatment | Extent of disease (mm) |
|---|---|---|
| RB | Control | 25.2$^a$ |
| RB | Hex-Am 1.5% | 0.7$^b$ |
| Reds | Control | 12.3$^a$ |
| Reds | Hex-Am 1.5% | 0.6$^b$ |
| Sup | Control | 7.7$^a$ |
| Sup | Hex-Am 1.5% | 0.9$^b$ |
| YG | Control | 6.8$^a$ |
| YG | Hex-Am 1.5% | 0.3$^b$ |
| RN | Control | 5.3$^a$ |
| RN | Hex-Am 1.5% | 1.0$^b$ |

Example 8

Protection of Wood from Termite-Induced Damage

Cedarwood oil (CWO) was extracted using carbon dioxide. All CWO carrier mixtures were formulated to contain 5% CWO by weight. The carrier mixture treatments were prepared using an electric hand blender by mixing on high for approximately 30 seconds. The five treatments tested were: Water Only; Ethanol Only (EtOH); 2% Hex-Am/2% PVOH; EtOH/CWO; and 2% Hex-Am/2% PVOH/CWO.

Using a no-choice test (i.e., only one treatment per container), vacuum impregnated wood blocks were tested for resistance to eastern subterranean termites, *Reticulitermes flavipes* (Kollar) (Isoptera: Rhinotermitidae) using Standard Method for Laboratory Evaluation to Determine Resistance to Subterranean Termites E1-06 (AWPAS, 2007).

Spruce/Pine/Fir (SPF) blocks were prepared from a board milled to 2.54 cm×2.54 cm×0.64 cm. The wood blocks were conditioned to a constant mass at 25° C. and 50% relative humidity (RH) and weighed prior to vacuum impregnation with the control and experimental compounds. After impregnation, the solvent was allowed to evaporate and the blocks re-conditioned to a constant mass at 25° C. and 50% RH. Weight loss was determined after a 4-week exposure to the termites. There were six replications of each treatment.

Figure 7:
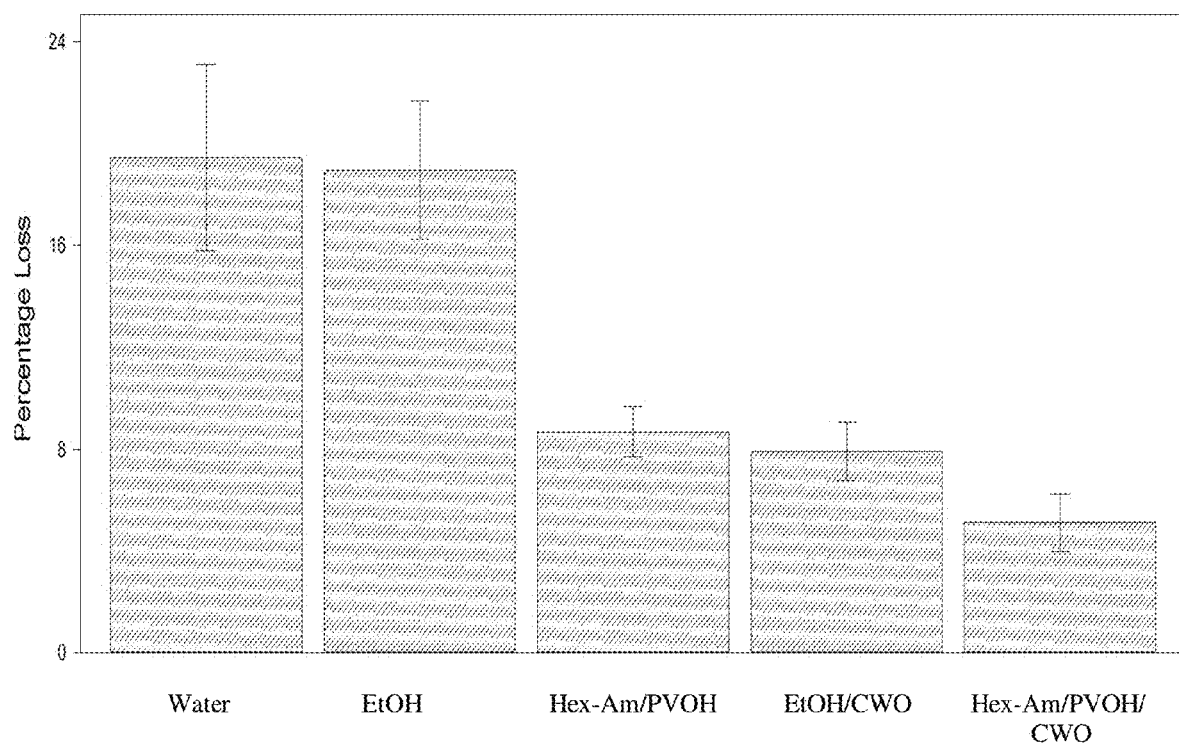
FIG. 7 provides graphic representation of the ability of Hex-Am/PVOH to deter termite feeding on treated wood. Percent weight losses for termite-exposed pine wood blocks treated with water, ethanol (EtOH), Hex-Am/PVOH, ethanol and cedar wood oil (CWO), and Hex-Am/PVOH and CWO are shown.

The results of the termite resistance tests are shown in FIG. 7. Percent weight losses were highest for the Water & EtOH treatments. The lowest observed mean weight loss was for the 2% Hex-Am/2% PVOH/CWO treatment which was statistically equivalent to the EtOH/CWO & 2% Hex-Am/2% PVOH treatments. The 2% Hex-Am/2% PVOH treatment had inhibitory effects towards termites in the absence of CWO. The 2% Hex-Am/2% PVOH treatment also decreased both water absorption and swelling.

Additionally, increased termite mortality was noted for the test samples. The percentage of termite mortality was lowest for the water (54.3%) and EtOH (41.3%) treatments and these two treatments were statistically equivalent. The highest termite mortalities were for 2% Hex-Am/2% PVOH/CWO (100%), EtOH/CWO (97.6%) and the 2% Hex-Am/2% PVOH (94.5%) treatments. Termite mortalities for these three treatments were statistically higher than both the mortalities for the water and EtOH treatments, but were statistically equivalent to one another.

Example 9

Protection of Grape Vine Cuttings from Microbial Infection

Tests on grape vine cutting were performed to determine the ability of the amylose-N-hexadecylammonium chloride inclusion complex blended with polyvinyl alcohol (133 k Mw) to prevent the growth of the fungal pathogens *Eutypa lata* and *Cytospora*. For preparation of the solutions, the N-hexadecylammonium chloride amylose inclusion complex (Hex-Am) was dispersed in water with polyvinyl alcohol (PVOH: 133,000 m.w., 99% hydrolyzed) at a 2% solution in water, which required heating to 80° C. followed by cooling. Grape cuttings were collected and coated with the 2% Hex-Am/PVOH solution or water as a control. The cuttings were then placed in a container containing spores the fungal pathogens *Eutypa lata* and *Cytospora*. The efficacy of the fungal pathogen was determined by monitoring the percent coverage of the pathogenic fungus on the pruning wound by visual inspection after 40 days (Table 6). The application of the Hex-Am/PVOH complex significantly reduced the fungal growth.

TABLE 6

Protection of grape vine wounds against fungal pathogens by Hex-Am/PVOH

| | |
|---|---|
| Control - Water | |
| *Eutypa Lata* | 100% growth |
| *Cytospora* | 70% growth |
| Hex-Am/PVOH (2% solution 1:1 ratio) | |
| *Eutypa Lata* | 7% growth |
| *Cytospora* | 3% growth |

Example 10

Antimicrobial Susceptibility Testing of Treated Articles

The amylose inclusion complexes utilized in these tests were using the microwave method described herein (*Starch* 2013, 65, 864-874). For the production of these ammonium salt complexes, high amylose corn starch was utilized (Amylomaize VII, 70% amylose) and obtained from Cargill, Minneapolis, Minn.

In order to define the ability treated materials containing N-hexadecylammonium chloride amylose inclusion complexes (produced in the standard fashion) to inhibit the growth of microbes on articles such as medical gauze and bandages, a panel of 7 microorganisms were selected and tested against paper and medical gauze surfaces. Approximately 0.5 cm$^2$ of each test article was treated aseptically with 25 µl of an autoclaved 2% solutions of N-hexadecylammonium chloride amylose inclusion complex (amount of N-hexadecylammonium chloride in complex was 7.5% of the amylose present in the starch) applied directly to the surface and allowed to completely dry prior to testing. The treated samples were allowed to dry in a sterile biological hood for 24 hours, afterwards the samples were placed in triplicate wells of 96 well plates. As a control, antibiotic bandages (pad cut into 0.5 cm$^2$) were included and tested as-is. The testing substrates used were—Medical gauze (Walgreens sterile gauze pad), paper (6 mm Blank paper disc—BBL Becton, Dickenson & Co., Sparks, Md.) and an antibiotic bandage—(Johnson and Johnson Band Aid™ with Neosporin).

The following representative organisms from ATCC culture collections were tested for antimicrobial susceptibility: *Aureobasidium pullulans* ATCC 58559, *Staphylococcus aureus* ATCC 29213, *Penicillium verruculosum* NRRL 1050, *Aspergillus niger* NRRL 3, *Escherichia coli* NRRL B-3054, *Pseudomonas aeruginosa* NRRL B-771, *Acinetobacter johnsonii* NRRL B-14921. Organisms were propagated individually on their recommended growth medium and at recommended temperature. All organisms were subcultured onto Sabouraud dextrose agar and grown 28° C. for 48 hours.

Yeast and bacterial inoculums were prepared by picking five colonies about 1 mm in diameter and suspending into 5 mL of sterile 0.85% saline to produce a 0.5 McFarland standard, vortexed, measured using a Bectin Dickinson CrystalSpec Nephelometer, and adjusted if necessary. A working suspension was prepared by diluting the stock solutions for each organism 100-fold into RPMI-1640 (RPMI-1640 medium supplemented with L-glutamine, 2% glucose, and buffered to pH 7.0 with 0.156 M 3-N-morpholinopropane-sulphonic acid (MOPS)).

The ability of the materials treated with N-hexadecylammonium chloride amylose inclusion complex test materials to inhibit microbial growth was determined using a broth micro-dilution assay (reference CLSI standard M27-A3). Testing was performed in 96 well flat-bottomed plates. Briefly, to each well, a working suspension (180 µL) of each organism was added in triplicate to each test material. The 96 well plates were incubated aerobically at 28° C. for 3 days; except after 64 hour incubation, samples of the media were removed and plated and then allowed to grow for 72 hours at 28° C. to assess if microbial growth occurred. Plates (72 hr) were scored and compared visually with the amount of growth in the growth control wells (no test material) for each organism where turbidity is an indication of microbial growth. For both OD600 measurements and visually scoring analysis methods, the MIC is the lowest concentration of test material that prevents visible growth of a given organism when compared to growth control wells containing 0% test material for each organism. Triplicate sterile control wells containing only RPMI-1640 broth for each test material and concentration was tested and remained optically clear. Results are shown in Table 7 ("+" signifies no visual microbial growth after 72 hours; "−" signifies visual growth after 72 hours).

TABLE 7

Antimicrobial effects of treated materials

| Organism | N-Hexadecylammonium chloride | | Control Triple Antibiotic bandage |
|---|---|---|---|
| | Medical gauze | Paper | |
| A. pullulans | + | + | + |
| P. verruculosum | + | + | − |
| A. niger | + | + | − |
| S. aureus | + | + | + |
| E. coli | − | − | − |
| P. aeruginosa | − | − | − |
| A. johnsonii | − | − | + |

Example 11

Process and Storage Stability Testing

In order to define the processing parameters of N-hexadecylammonium chloride amylose inclusion complexes and their ability to inhibit the growth of microbes, a panel of 5 microorganisms with varying degrees of susceptibility were selected and tested. Solutions of N-hexadecylammonium chloride amylose inclusion complexes were prepared through microwave production, and either tested immediately following microwave production, freeze dried and subsequently redisspersed and autoclaved before testing, or freeze dried, redisspersed, autoclaved and stored for 6 months before testing. The macro-broth dilution MICs for each fungal, yeast, or bacterial organism was performed following the CLSI standard M27-A3 as the guideline and measuring OD600 on a microplate reader.

The amylose inclusion complexes utilized in these tests were made using microwave production as described herein. High amylose corn starch was utilized (Amylomaize VII, 70% amylose) and obtained from Cargill, Minneapolis, Minn. A Biotage Initiator Microwave Synthesis Systems (Biotage AB, Uppsala, Sweden) microwave reactor oven was used to irradiate ~3% solids (m/m) mixtures of starch and N-hexadecylammonium chloride in deionized water. The N-hexadecylamine was added to the starch, and was converted to the ammonium chloride salt by adding an equal molar amount of 1.035 M HCl. The solution was pre-stirred for 1 minute with a Teflon magnetic stir bar at maximum speed. The sample was heated from 20 to 140° C. in 1.5 min, after which the reaction vessel maintained a temperature of 140° C. for 10 min. The reactor vessel was then cooled until the sample reached room temperature. Samples were then utilized immediately for antimicrobial testing or centrifuged for 20 minutes at 1,400×g and the supernatant was collected and freeze dried using a Labconco Freezone 6 Liter freeze dryer (Labconco, Kansas City, Mo.).

Test materials were 2% aqueous solutions of N-hexadecylammonium chloride inclusion complexes. In all examples, N-hexadecylammonium chloride amylose inclusion complex was used as the agent. The amount of N-hexadecylammonium chloride present in the starch sample was 7.5% of the amylose present in the ~70% amylose starch material.

The N-hexadecylammonium chloride amylose inclusion complex was either utilized directly after microwave production or the freeze-dried samples were dispersed in water to give a 2% solution. This solution was prepared by heating to 80° C., on reaching 80° C., the now clear solution was cooled quickly to room temperature by cooling in an ice bath. Samples were subsequently autoclaved and either used immediately after autoclaving or stored for 6 months at room temperature prior to antimicrobial testing.

The following representative organisms from ATCC culture collections were tested for antimicrobial susceptibility: Aureobasidium pullulans ATCC 58559, Staphylococcus aureus ATCC 29213, Penicillium verruculosum NRRL 1050, Aspergillus niger NRRL 3, Acinetobacter johnsonii NRRL B-14921. Organisms were propagated individually on their recommended growth medium and at recommended temperature. All organisms were subcultured onto Sabouraud dextrose agar and grown 28° C. for 48 hours.

Yeast and bacterial inoculums were prepared by picking five colonies about 1 mm in diameter and suspending into 5 mL of sterile 0.85% saline to produce a 0.5 McFarland standard, vortexed, measured using a Bectin Dickinson CrystalSpec Nephelometer, and adjusted if necessary. A working suspension was prepared by diluting the stock solutions for each organism 100-fold into RPMI-1640 (RPMI-1640 medium supplemented with L-glutamine, 2% glucose, and buffered to pH 7.0 with 0.156 M 3-N-morpholinopropane-sulphonic acid (MOPS)).

The ability of the N-hexadecylammonium chloride amylose inclusion complexes to inhibit microbial growth was determined using a broth micro-dilution assay (reference CLSI standard M27-A3). Testing was performed in 96 well flat-bottomed plates. Briefly, 20 μL of test solution was pipetted aseptically into designated triplicate wells of 96 well plates. Working suspension (180 μL) of each organism was added in triplicate to each concentration of each test material. Optical densities at 600 nm (OD600) were measured on a SpectraMax M2 plate reader (Molecular Devices) at 0 hr. The 96 well plates were incubated aerobically at 28° C. for 3 days. After 64 hour incubation, OD600 was again measured on each plate to determine if the growth of the microbes was inhibited. Triplicate sterile control wells containing only RPMI-1640 broth for each test material and concentration was tested and remained optically clear. For certain tests, visual examination of the plates was made.

For both OD600 measurements and visually scoring analysis methods, the MIC is the lowest concentration of test material that prevents visible growth of a given organism when compared to growth control wells containing 0% test material for each organism. Triplicate sterile control wells containing only RPMI-1640 broth for each test material and concentration was tested and remained optically clear.

The results of the antimicrobial tests of the various compounds are shown below in Table 9. Minimum inhibitory concentration (MIC) was determined as the lowest concentration of the test solution that resulted in lack of any turbidity. Where a value is not shown, then the range in percent reduction in observed growth (turbidity) at 0.04 is shown, unless otherwise specified (with >0.04 indicating no reduction in turbidity at any tested concentration).

TABLE 8

Antimicrobial effects of treated materials

N-Hexadecylammonium chloride

| Organism | Complex solution used immediately after preparation (MIC) | Freeze-dried complex, re-dissolved, used immediately (MIC) | Freeze-dried complex, re-dissolved, stored 6 months (MIC) |
| --- | --- | --- | --- |
| A. pullulans | 0.008 | 0.008 | 0.008 |
| P. verruculosum | 0.008 | 0.008 | 0.008 |
| A. niger | 0.04 | 0.04 | 0.04 |
| S. aureus | 0.008 | 0.008 | 0.008 |
| A. johnsonii | 50-95% | 50-95% | 50-95% |

While the invention has been described with reference to details of the illustrated embodiments, these details are not intended to limit the scope of the invention as defined in the appended claims. The embodiment of the invention in which exclusive property or privilege is claimed is defined as follows:

What is claimed is:

1. A composition comprising a wood board or wood block impregnated with a fatty-amine polysaccharide inclusion complex, wherein the wood board or wood block is impregnated with the fatty-amine polysaccharide inclusion complex under vacuum pressure and wherein the impregnated wood board or wood block is more toxic to termites than a wood board or wood block lacking the fatty-amine polysaccharide inclusion complex.

2. The composition of claim 1, wherein the polysaccharide portion is amylose derived from high amylose corn starch.

3. The composition of claim 1, wherein the fatty amine portion of the inclusion complex is derived from one or more fatty ammonium salts, wherein each fatty ammonium salt comprises eight to twenty-two carbons in at least one chain attached to a nitrogen.

4. The composition of claim 3, wherein the one or more fatty ammonium salts comprise twelve to eighteen carbons.

5. The composition of claim 1, wherein the fatty amine portion of the inclusion complex comprises an amine with two carbon chains attached to a nitrogen and wherein the two chains attached to the nitrogen comprise eight carbons or less.

6. The composition of claim 1, wherein the fatty-amine portion of the inclusion complex is derived from a primary, secondary, or tertiary amine.

7. The composition of claim 6, wherein the amine is a secondary or tertiary amine comprising a first chain of twelve or more carbons, and wherein the second and third alkyl groups attached to the nitrogen have three or fewer carbons and wherein the second and third alkyl groups do not comprise hydroxyl groups.

8. The composition of claim 1, wherein the fatty amine portion of the inclusion complex is derived from a fatty ammonium salt selected from the group consisting of N-octadecylammonium chloride, N-dodecylammonium chloride, N,N-didecyl-N-methylammonium chloride, N-tetradecylammonium chloride, N-hexadecylammonium chloride, N,N-dioctylammonium chloride, N-dodecylanilium chloride, N-methyl-N-octadecylammonium chloride, N,N-dimethyl-N-hexadecylammonium chloride, N,N,N-trimethyl-N-tetradecylammonium chloride, N-hexadecyl-N,N,N-trimethylammonium bromide, benzethonium chloride, N-hexadecylpyridinium chloride, and N-laurylcholine chloride.

9. The composition of claim 8, wherein the fatty ammonium salt is N-hexadecylammonium chloride and is present at a concentration of 3-15% of the polysaccharide portion of the inclusion complex.

10. The composition of claim 9, wherein the polysaccharide portion of the inclusion complex is amylose.

11. The composition of claim 1, wherein the inclusion complex further comprises a film-forming agent, a plasticizer, or a combination thereof.

12. The composition of claim 11, wherein the film-forming agent is poly(vinyl) alcohol.

13. A method of decreasing insect consumption of wood, comprising exposing a wood eating insect to the composition of claim 1 under conditions which the insect would normally consume some or all of the wood, thereby decreasing the consumption of the wood as compared to wood lacking a fatty-amine polysaccharide inclusion complex.

14. The method of claim 13, wherein the insect is a termite.

* * * * *